(12) United States Patent
Osorio

(10) Patent No.: US 10,549,098 B2
(45) Date of Patent: Feb. 4, 2020

(54) METHOD, SYSTEM AND APPARATUS FOR AUTOMATED TERMINATION OF A THERAPY FOR AN EPILEPTIC EVENT UPON A DETERMINATION OF EFFECTS OF A THERAPY

(71) Applicant: FLINT HILLS SCIENTIFIC, LLC, Lawrence, KS (US)

(72) Inventor: Ivan Osorio, Leawood, KS (US)

(73) Assignee: FLINT HILLS SCIENTIFIC, LLC, Lawrence, KS (US)

( * ) Notice: Subject to any disclaimer, the term of this patent is extended or adjusted under 35 U.S.C. 154(b) by 107 days.

(21) Appl. No.: 15/367,757

(22) Filed: Dec. 2, 2016

(65) Prior Publication Data

US 2017/0143963 A1    May 25, 2017

Related U.S. Application Data

(60) Division of application No. 13/280,178, filed on Oct. 24, 2011, now Pat. No. 9,533,147, which is a
(Continued)

(51) Int. Cl.
| | |
|---|---|
| *A61N 1/36* | (2006.01) |
| *A61B 5/00* | (2006.01) |
| *A61F 7/12* | (2006.01) |
| *A61N 2/00* | (2006.01) |
| *A61N 5/06* | (2006.01) |

(Continued)

(52) U.S. Cl.
CPC ........ *A61N 1/36064* (2013.01); *A61B 5/4094* (2013.01); *A61B 5/4836* (2013.01); *A61B 5/4848* (2013.01); *A61F 7/12* (2013.01); *A61N 1/36114* (2013.01); *A61N 1/36139* (2013.01); *A61N 1/36142* (2013.01); *A61N 1/36146* (2013.01); *A61N 2/002* (2013.01); *A61N 2/006* (2013.01); *A61N 5/0622* (2013.01); *A61N 1/0529* (2013.01); *A61N 1/3621* (2013.01)

(58) Field of Classification Search
CPC ............ A61N 1/36064; A61N 1/36139; A61N 2/002; A61N 2/006; A61B 5/4094; A61B 5/4836; A61B 5/4848
See application file for complete search history.

(56) References Cited

U.S. PATENT DOCUMENTS

| | | | | |
|---|---|---|---|---|
| 2004/0133119 | A1* | 7/2004 | Osorio | A61B 5/048 600/544 |
| 2007/0150024 | A1* | 6/2007 | Leyde | A61B 5/0476 607/45 |
| 2009/0082640 | A1* | 3/2009 | Kovach | A61B 5/04001 600/300 |

* cited by examiner

*Primary Examiner* — Amanda K Hulbert
*Assistant Examiner* — Natasha Patel
(74) *Attorney, Agent, or Firm* — CF3; Stephen Eisenmann

(57) ABSTRACT

A method comprising detecting an epileptic event in a patient; applying an electrical therapy to a first target area in at least one of a brain region or a cranial nerve of said patient in response to said detecting; receiving a body signal responsive to the electrical therapy, wherein said body signal is selected from an autonomic signal, a neurologic signal, a metabolic signal, an endocrine signal, or a tissue stress marker signal; determining whether said body signal indicates that said electrical therapy has an efficacious effect; and terminating the application of said electrical therapy if the response indicates that the electrical therapy has an efficacious effect. An apparatus capable of performing the method. A non-transitive, computer-readable storage device for storing data that when executed by a processor, perform the method.

6 Claims, 11 Drawing Sheets

Related U.S. Application Data continuation-in-part of application No. 12/272,093, filed on Mar. 22, 2010, now Pat. No. 8,560,073.

(60) Provisional application No. 61/210,850, filed on Mar. 23, 2009.

(51) Int. Cl.
*A61N 1/05* (2006.01)
*A61N 1/362* (2006.01)

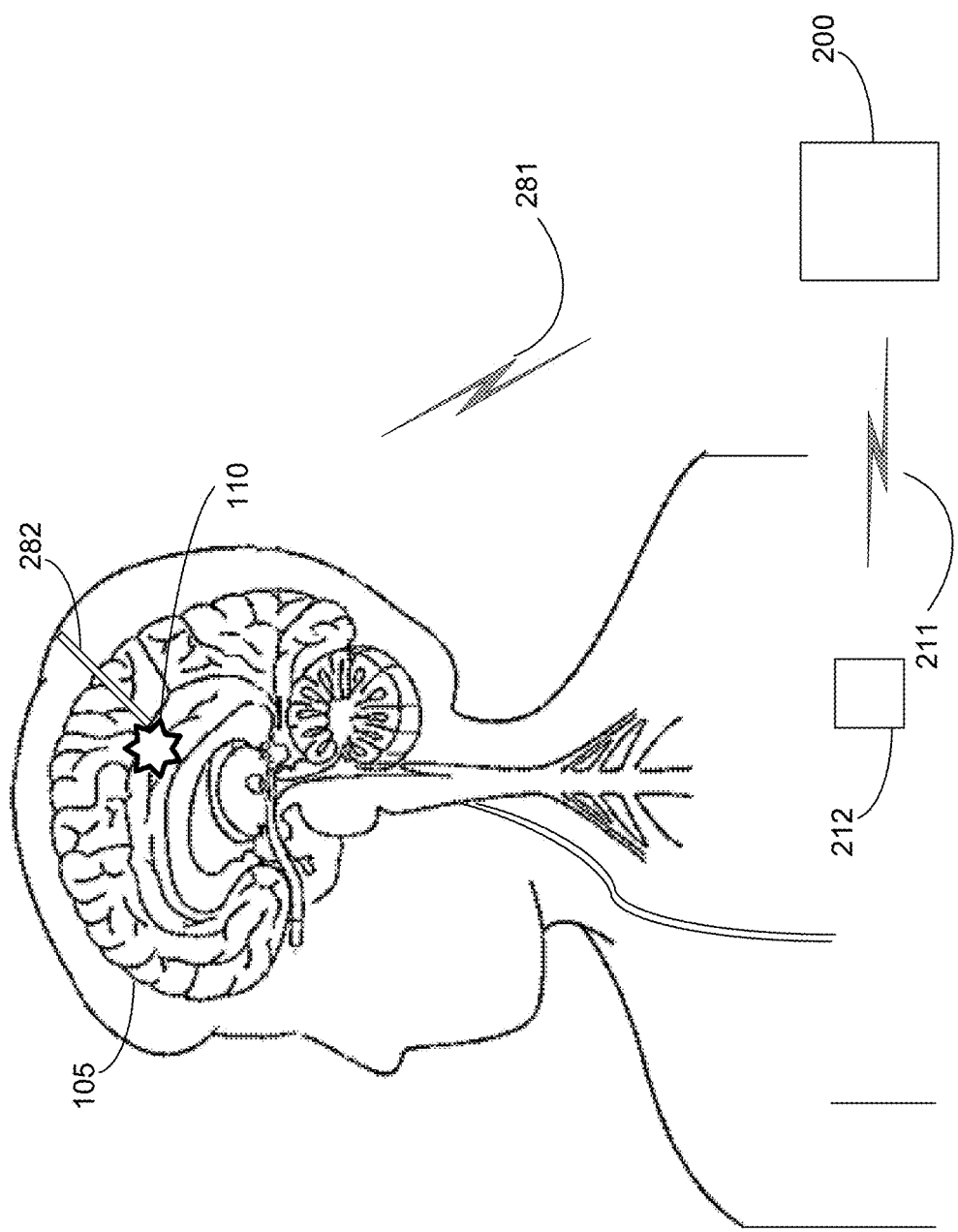

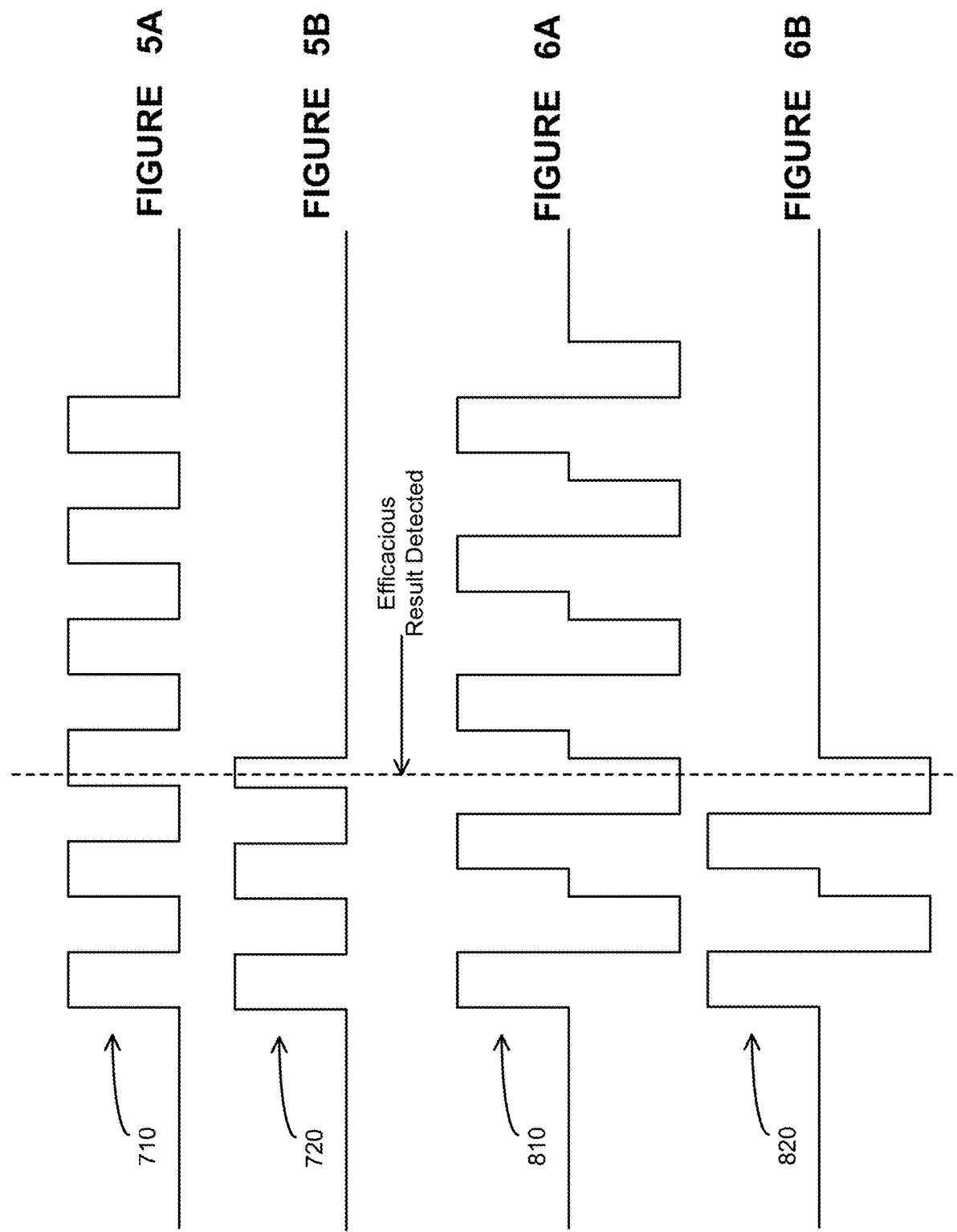

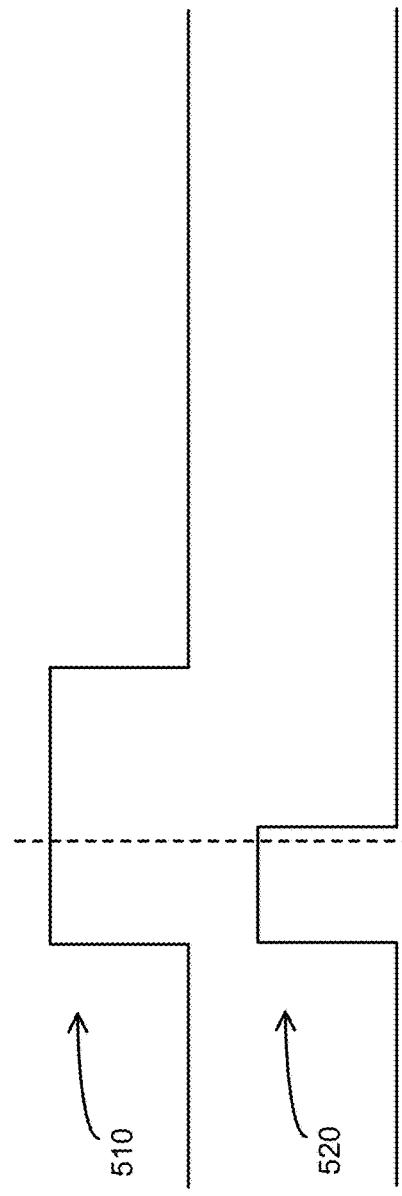
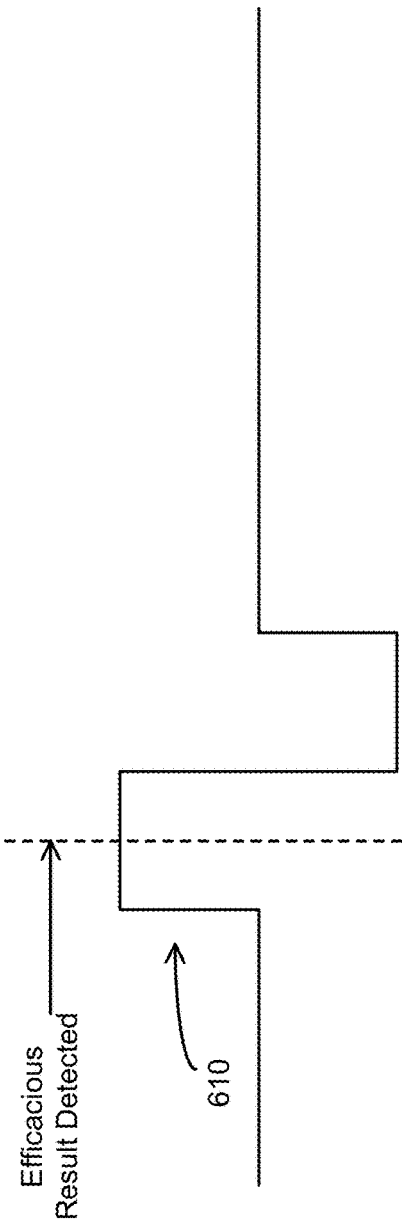
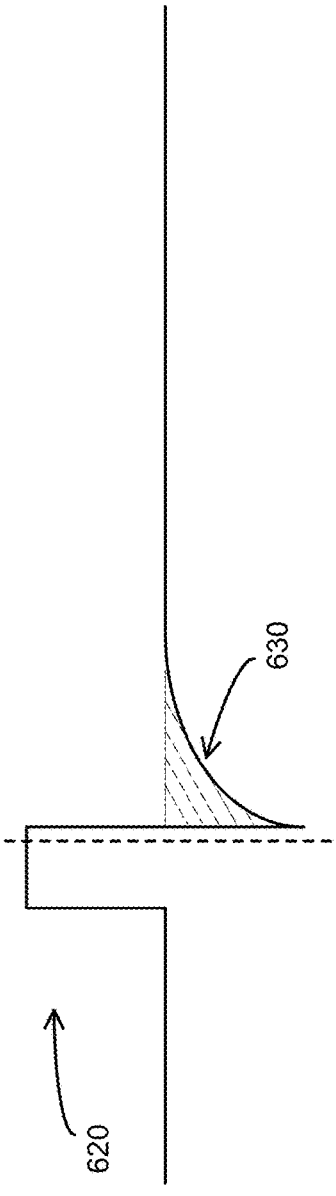

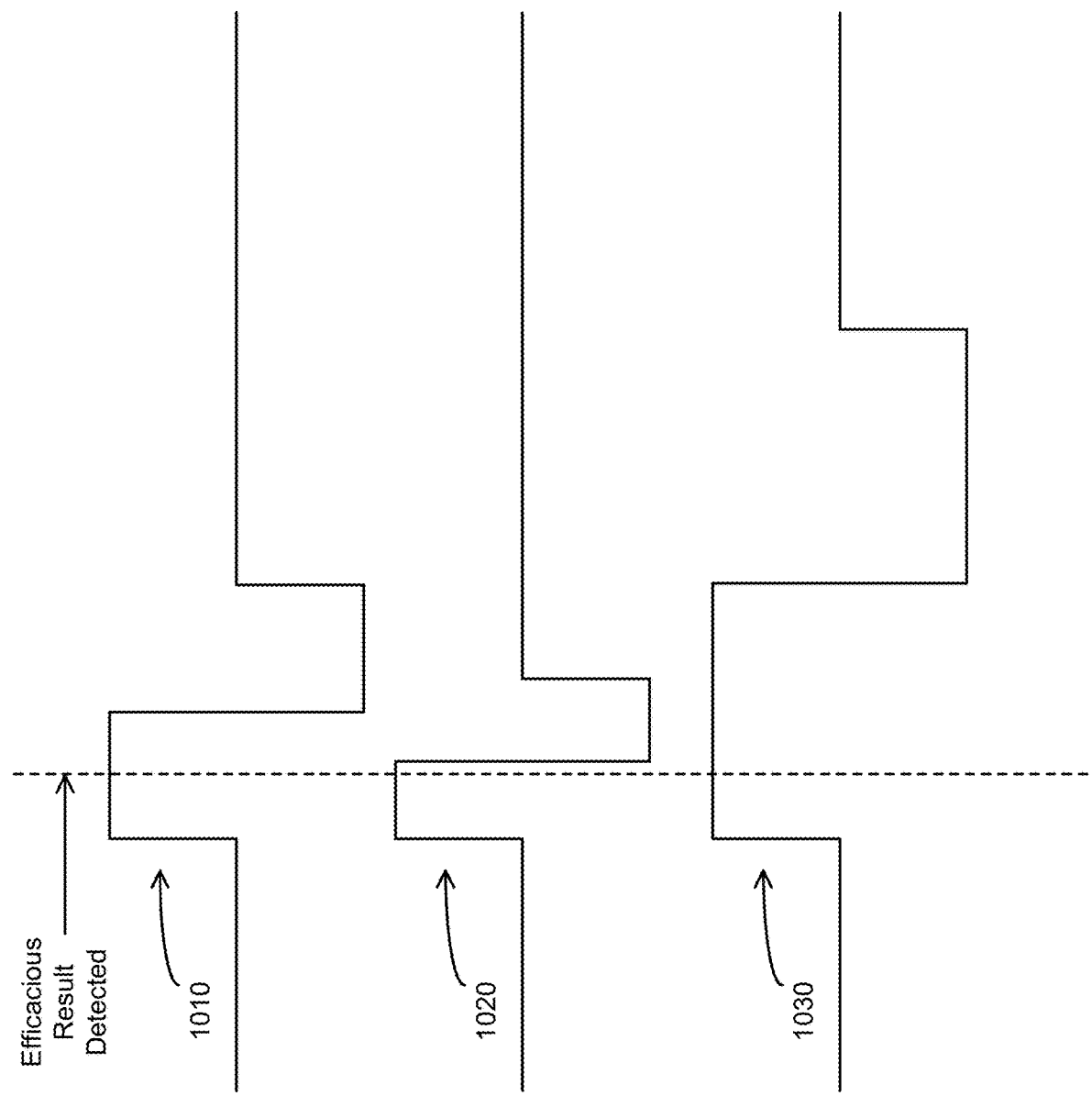

METHOD, SYSTEM AND APPARATUS FOR AUTOMATED TERMINATION OF A THERAPY FOR AN EPILEPTIC EVENT UPON A DETERMINATION OF EFFECTS OF A THERAPY

CROSS-REFERENCE TO RELATED APPLICATIONS

This application is a divisional of co-pending application Ser. No. 13/280,178 filed Oct. 24, 2011, which is a continuation-in-part of U.S. Ser. No. 12/729,093 filed Mar. 22, 2010, now U.S. Pat. No. 8,560,073, which claims priority to Provisional Application No. 61/210,850, filed Mar. 23, 2009.

BACKGROUND OF THE INVENTION

This application is a continuation-in-part of U.S. patent application Ser. No. 12/729,093, entitled "System and Apparatus for Automated Quantitative Assessment, Optimization and Logging of the Effects of a Therapy," filed Mar. 22, 2010 and currently pending, which claimed priority from co-pending U.S. provisional patent application No. 61/210,850, entitled "System and Apparatus for Automated Quantitative Assessment, Optimization and Logging of the Effects of a Therapy," filed Mar. 23, 2009. U.S. patent application Ser. No. 12/729,093 and 61/210,850 are hereby incorporated herein by reference in their entirety.

FIELD OF THE INVENTION

Safe and effective therapies for pharmaco-resistant seizures are a major unmet medical need affecting approximately 36% of all ~1.1 million US and ~18 million worldwide epileptics. These subjects have poor quality of life, with high rates of unemployment and depression. They are 40 times more likely to die suddenly than age-matched subjects in the general population. Brain electrical stimulation, either directly (e.g., deep brain stimulation) or indirectly (vagus nerve stimulation), and contingent (triggered by the onset of seizures) or non-contingent (e.g., periodic, round-the-clock), and other therapies such as localized cooling of the epileptogenic zone or direct delivery of drugs to it, hold great promise. However, in light of the results of large recent clinical trials showing a modest mean decrease in seizure frequency of 40-60% on patients that remain on multiple anti-seizure drugs, optimization is required for such therapies to meet efficaciously and cost-effectively this medical need. This disclosure addresses the complex and demanding task of optimization of interventional brain therapies for control of undesirable changes of state, particularly for brain state changes such as epileptic seizures. Therapies for other neurological (e.g., pain, movement), psychiatric (e.g., mood; obsessive compulsive), and cardiac (e.g., arrhythmias) disorders using other therapy modalities (e.g., drugs, thermal energy may be optimized using the approaches described herein.

Epileptic seizures occur with or without discernible or visible clinical manifestations. In the case of seizures originating from discrete brain regions (known as partial or "focal" seizures) the electrical abnormalities usually precede the first clinical manifestation (subjective or objective) and in a large number of these patients, impairment or loss of responsiveness occurs some time after the first clinical manifestation. Also, if the seizure becomes secondarily generalized, loss of consciousness occurs after loss of responsiveness. Commonly, abnormal electrical activity outlasts the loss of consciousness, and consciousness is regained before responsiveness returns to normal (for the patient) levels. In certain epileptic brains the transition from the non-seizure to the seizure state may be gradual, providing a window for prediction and intervention before the transition to the ictal state is complete. Degree of responsiveness may be tested and quantified in real-time using a wide variety of available tests.

Therapy for control of disorders such as epilepsy are especially challenging, because they manifest intermittently, aperiodically and briefly (ranging from seconds to rarely >2 min) and are classified as dynamic, meaning that state changes (from normal to abnormal and vice-versa) are caused by changes in the system's control parameter(s). To increase the probability of therapeutic success local, global, structural, dynamical, and state factors influencing the state change, must be identified and measured with useful precision and at informative time scales. These concepts and considerations, which influence treatment and optimization strategies, are lacking in the state-of-the art therapies.

While this disclosure is aimed at optimizing a therapy, nothing in its specification precludes delivery of a therapy prior to optimization or without optimization. Indeed, optimization cannot take place if a therapy has not been administered and its effects (beneficial and detrimental) noted and/or quantified. If a therapy cannot be optimized (in terms of increasing its beneficial effects), optimization may be effected by decreasing the number or intensity and duration of its adverse events. Adverse effects include but are not limited to unsafe effects and effects that are difficult for the patient to tolerate (e.g., discomfort but no damage to tissue). Unsafe effects may include effects involving worsening of the detected seizure or damage to brain or neural tissue. These adverse effects may be quantified using cognitive, electrical, thermal, optical and other signals and logged to computer memory. Signals that lack easily detectable or recognizable electrical or other correlates may be characterized using a semi-quantitative approach such as psychiatric scales, care-giver observations or patient diaries.

The term "therapy" may be interchangeably used with the term control for which a theory exists (Control Theory) in the field of engineering. Since therapy and control share the same aim, it is appropriate to adopt certain concepts form this theory as well as from the fields of dynamics to generate a rational approach and strategy for the management of pharmaco-resistant seizures.

The epileptic brain may be conceptualized as a non-stationary, non-linear, "noisy" system that undergoes sudden unexplained reversible transitions from the non-seizure state. These transitions may be "gradual" (through a process of "attractor deformation") or sudden (through a "leap" from one state to another) as observed in bi-stable or multi-stable systems. Dynamical theory teaches that a system may be defined by its dimension (i.e., the minimum number of variables required to specify it). The identification of a system's dimension greatly benefits from the identification of a spatio-temporal scale of observation that corresponds to a representative sample of the system (so-called mesoscopic scale), thus obviating the need to study the whole system at all scales, a daunting and impracticable task in the case of the mammalian brain. The epileptic brain's dimensionality and its mesoscopic scale have not been effectively specified to date. This knowledge void forces the treatment of the brain as a "black-box".

While by definition a "black-box" is not amenable to direct inquiry, it can be indirectly studied through perturbations of system inputs. A known, well characterized input is "fed" into the "black-box" and the output is carefully recorded and characterized quantitatively or qualitatively and compared to the input. Transformations, if any, to the input properties provide indirect but useful information about the "black-box" that may be captured mathematically as transfer functions. For example, if doubling the amplitude of the input translates into doubling of the output, the system is considered linear. However if doubling the input causes an exponential increase in the output, the system is non-linear (likely the brain's case). If sine waves are fed into the black box and 60 Hz. activity appear on them as they exit the box, it is reasonable to infer that the box corrupts the waves and is "noisy". Successful control of the behavior of "black-boxes" cannot occur if the measurements of its output are not representative of the state(s) and site(s) from where they are obtained, reasonably precise and also reproducible from measurement to measurement.

Global and local factors (many state-dependent) also shape the response to therapies. For example, the rate and direction of diffusion of particles and molecules in animal tissue (e.g. brain), depends on multiple factors including size, chemical valence and the size and tortuosity of the extracellular space. In certain tissues, such as the brain, the average values of the dielectric constant, or permittivity, and of the resistance are not equal at all points of the volume which the particles and molecules occupy. This anisotropy, which varies by a factor of 5-10 between two orthogonally-selected directions, such as between the vertical (or radial) and horizontal (or transverse) directions in a brain's cortex or its axons, ensures that diffusion of endogenous and exogenous (e.g., electrical stimulation) currents is not homogenous. This lack of homogeneity (and of isotropy) in the case of a therapy (e.g., electrical stimulation) that must diffuse through the tissue to exert its beneficial action is likely to decrease efficacy, a feature that must be considered for control and optimization purposes.

The diffusions of electrical currents within the brain, which as vectors have both magnitude (potential) and direction, are the result of electrostatic forces caused by the transient accumulation of charges, and electrodynamic actions arising from ionic or electronic currents in the volume which surrounds the local accumulations of such charges. Intracortical diffusion of electrical charges (ions) and currents, takes place at several spatial domains or scales (active membrane sites, cells, columns and the cortical synergic groups where they flow differentially through the lattice of intercellular spaces and through the network of glial cells. These flows occur through a multiplicity of paths, each accounting for only a small part of the total current (Kirchhoff's law), a "fractionation" that may result in insufficient (or excessive) current densities and low or no efficacy or adverse effects in certain sites.

An additional challenge to controlling brain state changes is that tissue anisotropy is not uniform or constant but varies as a function of differences in cortical cytoarchitecture and the state of activation within the volume where endogenous or exogenous currents diffuse. These inter-regional or areal differences translate into time- and space-constant differences that make the probability of generation of action potentials and their conduction velocities behave differentially. When present, these differences lead to the spatio-temporal dispersion of endogenous or exogenous (e.g., electrical stimulation) currents and to a lower than desirable current flux through the region of interest—and thus potentially to loss of therapeutic efficacy. However, the opposite may also occur and current flux may be higher than desirable for efficacious control or safety purposes.

The fact that electrical currents both trigger and control seizures depending on the stimulation parameters used, such as frequency and intensity, among many other factors, should be considered for therapeutic purposes. In addition to the inherent widespread morphological or structural anisotropy of nervous tissue, diffusion of electrical potentials also depend on: a) the state (at both global and local levels and at long and short time scales) of the network; b) on the level (spike frequency) and pattern of spike activity and the "valence" (inhibitory or excitatory) of inputs and outputs, which are likely reflected in changes in tissue conductivity/diffusivity and responsivity to both endogenous and exogenous currents. For example, tissue resistivity is altered by bursts of epileptiform discharges of only a few seconds duration and frequent seizures often alter tissue osmolality, both of which are likely to negatively impact therapeutic efficacy, unless these factors are taken into account and/or measured.

As for electrical stimulation, the most investigated therapeutic modality for pharmaco-resistant epilepsies, the electric field $E_i$, at every point i on the surface of a charged needle (which closely approximates in shape the deep brain electrodes used in humans for treatment purposes) is similar to the set of diffusion limited aggregation growth probabilities and in this sense, the electric field $E_i$, is also a multi-fractal set. This means that different "regions" in the electric field (and by extension in the tissue where the field is active) are not only fractal but have different fractal values or properties at different points. That an electric field as described above is a multi-fractal set brings to the fore one of the central themes of this work, the spatio-temporal "inhomogeneity" of a therapy (electrical) and the requirement (for optimization of this treatment modality) to apply concepts (from multi-fractal theory, among others) to quantitatively characterize this complex phenomenon.

Prior art therapies also ignore the dampening and the linear and non-linear distortions of frequency, phase, harmonics and amplitude that invariably occur as currents travel through brain tissue. More specifically, prior art therapies and interventions for blocking, abating, or preventing undesirable state changes ignore tissue anisotropy, dielectric hysteresis, state and circadian influences at local and global scales and the changing nature (non-stationarity) in the type, pattern and level of neuronal activity as a function of state and time as reflected in intra-individual and inter-individual differences in seizures.

U.S. patent application Ser. No. 12/729,093 includes figures depicting the power spectrum (a representative estimation of brain activity) of neuronal activity recorded over 162 hours from the same site in the same human subjects. These figures demonstrate how the activity of the epileptogenic zone, as reflected in the power spectrum, changes as a function of time. The spectrograms and the temporal evolution of the values of a) the decimal logarithm of the standard deviation; b) the generalized Hurst exponent; and c) the singularity spectra width values of two seizures recorded from 11 subjects point clearly to the importance of tailoring therapy to intra- and inter-individual differences. It is improbable that electrical stimulation with fixed parameters (the state-of the-art as of the filing date of U.S. patent application Ser. No. 12/729,093) delivered to each of these seizures will have the same effect, let alone that it will be uniformly beneficial.

If seizure properties or features are determined using spectral methods and classified into clusters (each cluster represents a given type of seizure) using vectors of their properties (e.g., the log of the standard deviation, the singularity spectra width values, etc.), the inventor has found that there may be more than one cluster or seizure type for each subject (even for seizures originating from the same site), and that the number of clusters changes over time, suggesting corresponding changes in the number of main "modes" of neural activity. Seizures may have a latent circadian periodicity which may be extracted as periodicity in the variation of the pseudo-F-statistic maximum values. This periodicity may disappear as a function of time, state, and other factors. FIG. 9 depicts the time evolution of the values of the Pseudo-F statistic (a measure of cluster tightness) of seizures recorded from the same site and from the same individual. Red clouds seen at 1.2 (~12 hr) and 1.4 (~24 hr) in the y-axis (the log of time) and present from the start of the recording and indicative of a circadian tendency for seizure properties to cluster, that is, to be highly similar, vanish after approximately 110 hours (x-axis, time in hours) indicating the loss of the circadian trend. This observation further exposes the variability of abnormal brain activity over intermediate time scales (tens of hours), variability that may be detected and measured to optimize (as a function of time) therapeutic efficacy.

Other important factors that are ignored by current therapies are: (i) seizure blockage does not necessarily translate into prevention of loss of cognitive functions, the most disabling seizure symptom; (ii) the inherent and inevitable delay in arrival of the therapy to its target site, which depends among others on the therapeutic modality (relatively short for electrical currents and relatively long for drugs and thermal energy); (iii) the degree (low or high) of morphological similarity or rhythmicity among waves that make up a seizure, which determines the probability (high if the waves are highly similar) of seizure blockage, especially if electrical stimulation is the therapy of choice; (iv) the lack of uniformity in flow direction and in density of both the abnormal activity and the therapy, as well the differences in their speed of propagation, their synchronization levels and degree of rhythmicity.

SUMMARY OF THE DISCLOSURE

In one embodiment, the present disclosure provides a method, comprising: detecting an epileptic event in a patient based on at least one detection body signal selected from at least one of an autonomic signal, a neurologic signal, a metabolic signal, an endocrine signal, and a tissue stress marker signal; applying an electrical therapy to a first target tissue in at least one of a brain region or a cranial nerve of said patient in response to said detecting the event; receiving an efficacy body signal after applying the electrical therapy, wherein said efficacy body signal is selected from at least one of an autonomic signal, a neurologic signal, a metabolic signal, an endocrine signal, and a tissue stress marker signal; determining whether said efficacy body signal indicates that said electrical therapy has an efficacious effect; and terminating the application of said electrical therapy if the determining indicates that the electrical therapy has an efficacious effect.

In one embodiment, the present disclosure provides a medical device system, comprising: an epileptic seizure detection module configured to detect a first epileptic seizure based on at least one of a cardiac index and a kinetic index; a therapy module configured to apply a therapy to at least one target tissue of said patient based on an indication of said epileptic seizure; at least one sensor configured to collect one or more body signals from a patient's body; an efficacy determination module configured to receive said collected one or more body signals and detect a response of said epileptic event to said therapy, wherein said detection is based on said collected one or more body signals; and a therapy termination module configured to terminate said therapy based on an indication that said therapy has an efficacious effect, and to prohibit the application of the therapy until the occurrence of an event selected from a worsening of the first epileptic seizure, a relapsing of the first epileptic seizure, an end of the first epileptic seizure, the elapse of a re-initiation time period after the termination of the therapy, an onset of a second epileptic seizure, receiving an indication that a cumulative seizure severity index has been reached, receiving an indication that a cumulative seizure frequency index has been reached, receiving an indication that resumption of said electrical therapy does not exceed a predetermined current density stimulation limit, the time elapsed from the previous seizure is below a certain threshold, an indication that application of the electrical therapy will not result in an adverse effect, and receiving an indication of the lapse of a beneficial carryover effect.

In one embodiment, the present disclosure provides a method, comprising: detecting an epileptic event in a patient based on at least one of a cardiac index, a kinetic index, and a responsiveness index of the patient; applying an electrical signal therapy to a target tissue of the patient in response to said detecting; detecting at least one body signal after applying said electrical signal therapy, wherein said at least one body signal is selected from an autonomic signal, a neurologic signal, a metabolic signal, an endocrine signal, or a tissue stress marker signal; and determining an efficacy index based upon said feedback body signal; wherein the duration and parameters of the therapy are adaptively determined based on the efficacy index.

In one embodiment, the present disclosure provides a method, comprising: detecting a first epileptic seizure in a patient; applying a first electrical therapy to at least one target tissue of said patient for treating said first epileptic seizure; detecting at least one body signal after applying the electrical therapy, wherein said body signal is selected from an autonomic signal, a neurologic signal, a metabolic signal, an endocrine signal, or a tissue stress marker signal; determining whether said at least one body signal indicates that said electrical therapy has an efficacious effect; and terminating the application of said electrical therapy in response to a determination that said electrical therapy has an efficacious effect, and not resuming the application of said electrical signal therapy until the occurrence of an event selected from detecting a worsening of the first epileptic seizure, detecting a relapsing of the first epileptic seizure, detecting an end of the first epileptic seizure, the elapse of a re-initiation time period after the termination of the therapy, detecting the onset of a second epileptic seizure, and determining that a cumulative seizure severity index has been reached, determining an indication that a cumulative seizure frequency index has been reached, determining that resumption of said electrical therapy does not exceed a predetermined stimulation limit, determining that application of the electrical therapy will not result in an adverse effect, and determining that a beneficial carryover effect has lapsed.

In one embodiment, the present disclosure provides a non-transitive, computer-readable storage device for storing data that, when executed by a processor, perform a method described above.

BRIEF DESCRIPTION OF THE DRAWING FIGURES

FIG. 1A depicts a medical device system, comprising an electrode implanted in the brain of a patient, in accordance with one illustrative embodiment of the present disclosure.

Figure 2:
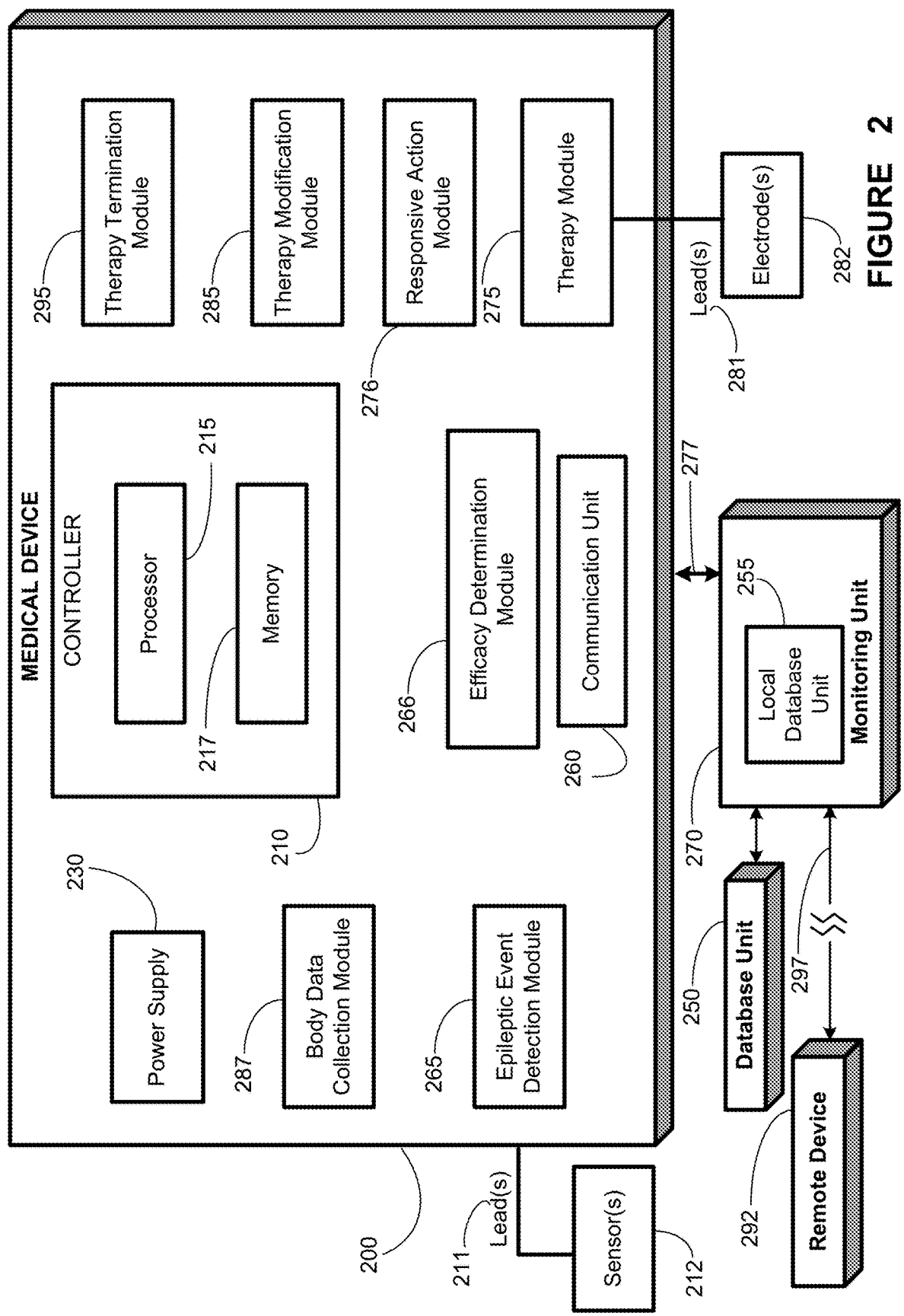

FIG. 2 presents a block diagram of a medical device system, in accordance with one illustrative embodiment of the present disclosure.

Figure 3A:
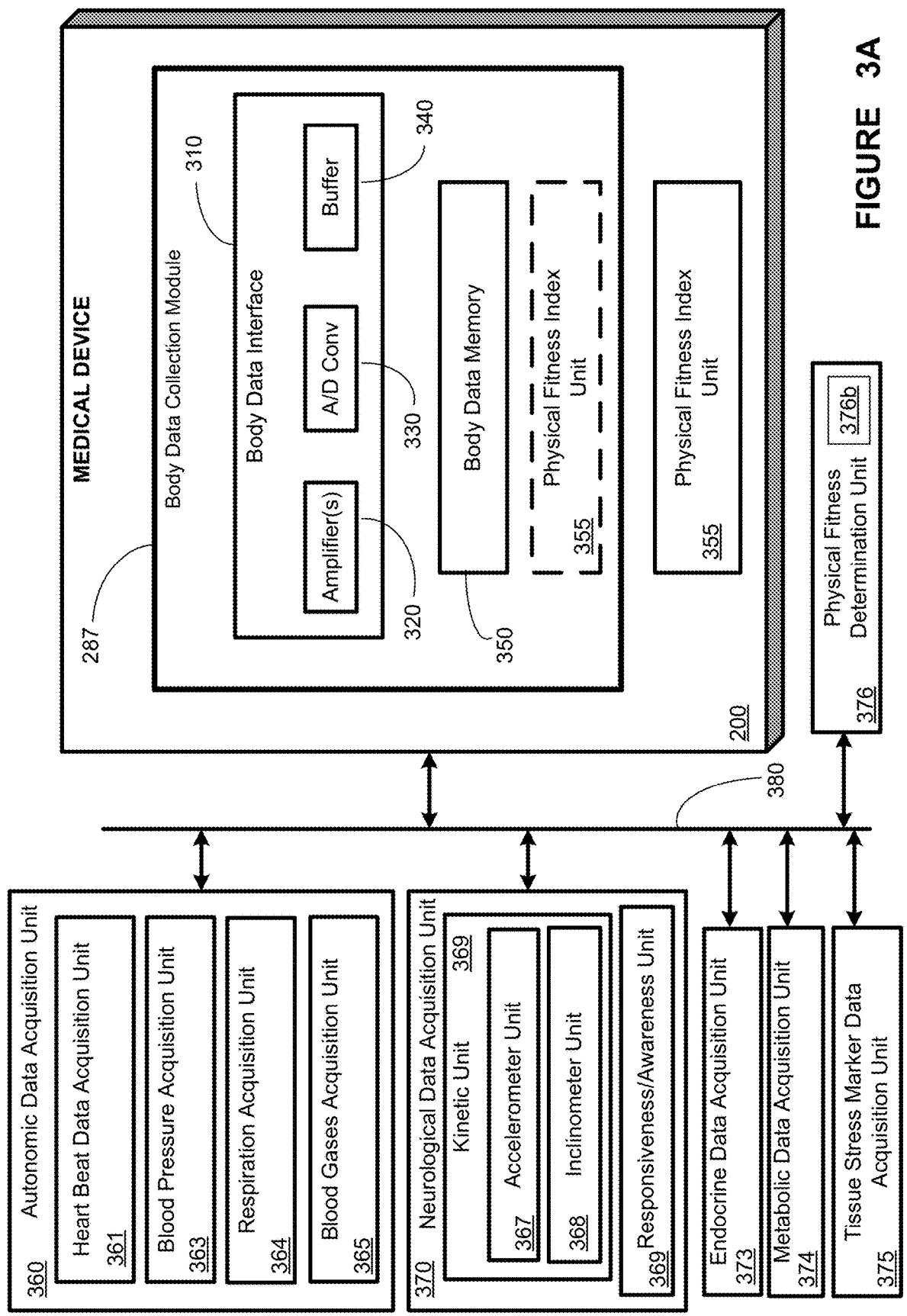

FIG. 3A presents a block diagram of a medical device system, in accordance with one illustrative embodiment of the present disclosure.

Figure 3B:
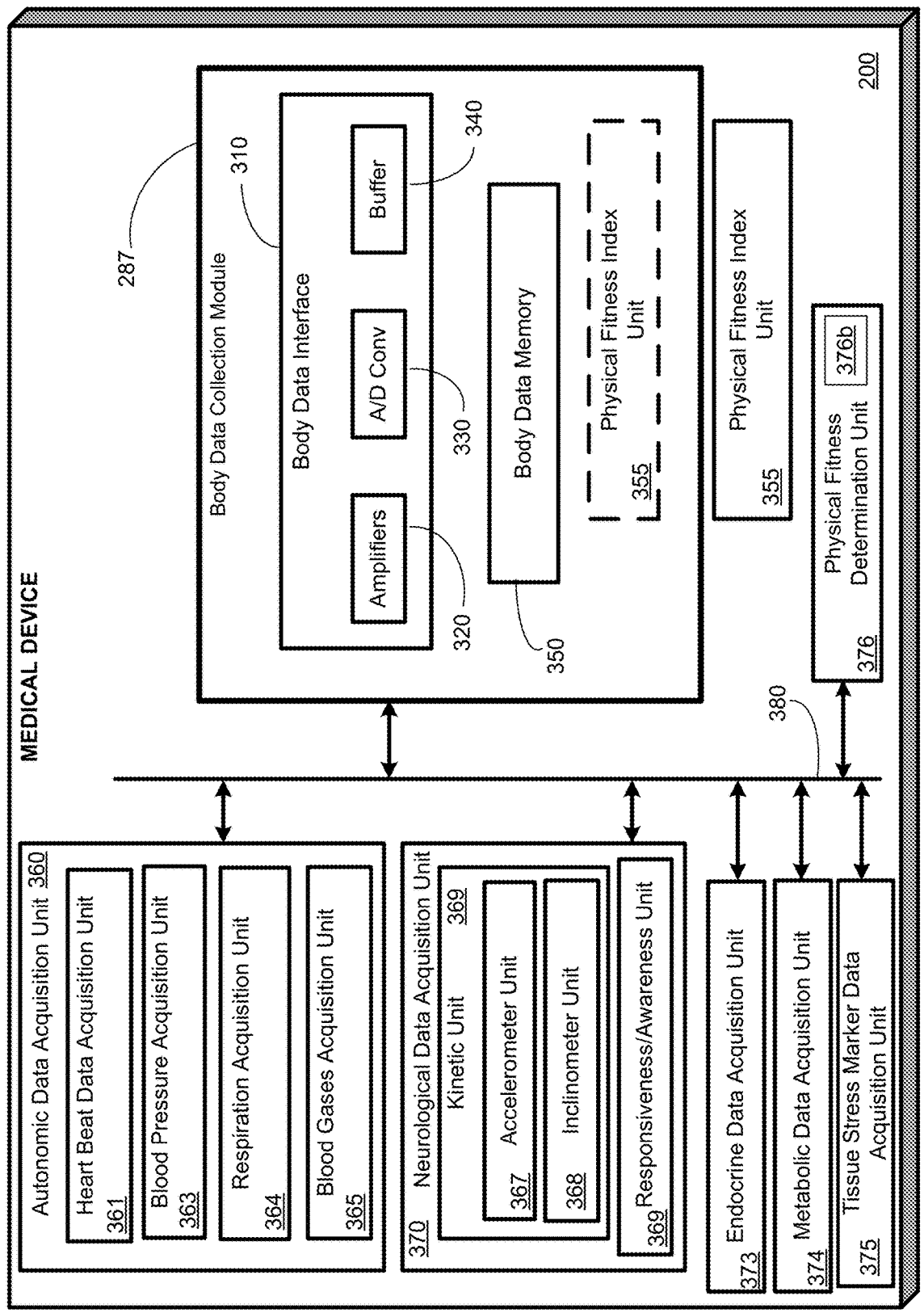

FIG. 3B presents a block diagram of a medical device system, in accordance with one illustrative embodiment of the present disclosure.

Figure 4:
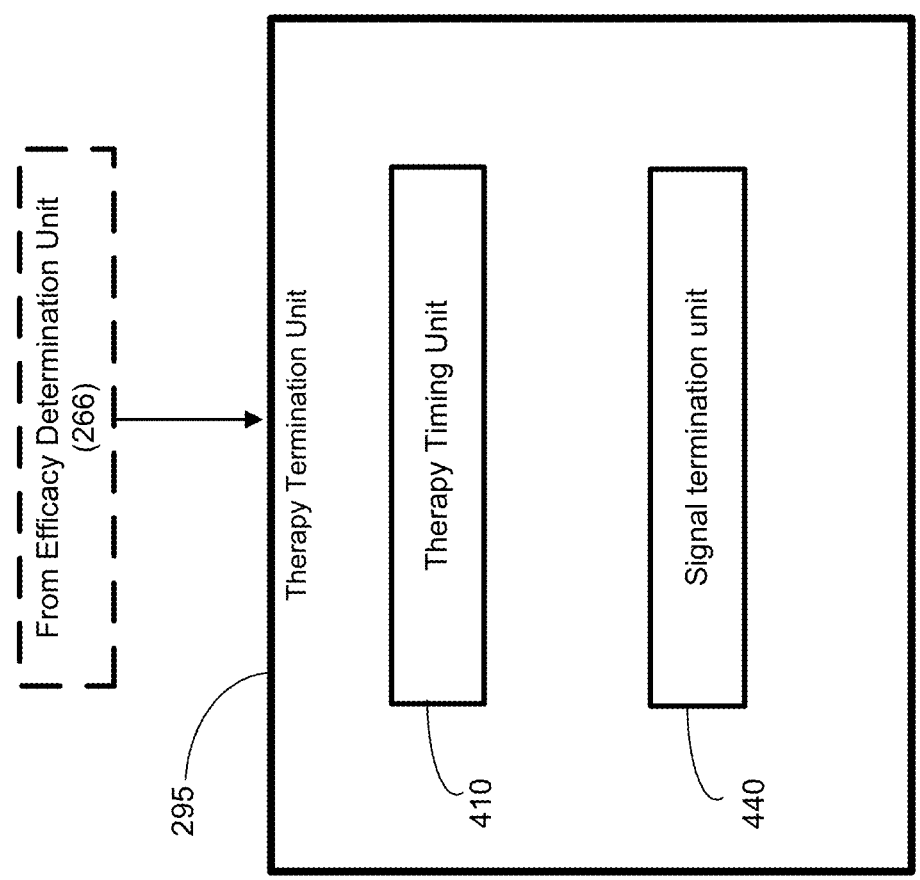

FIG. 4 presents a block diagram of a therapy termination unit of a medical device system, in accordance with one illustrative embodiment of the present disclosure.

FIG. 5A depicts an exemplary pulse signal and its termination, in accordance with one illustrative embodiment of the present disclosure.

FIG. 5B depicts an exemplary pulse signal and its termination, in accordance with one illustrative embodiment of the present disclosure.

FIG. 6A depicts an exemplary pulse signal and its termination, in accordance with one illustrative embodiment of the present disclosure.

FIG. 6B depicts an exemplary pulse signal and its termination, in accordance with one illustrative embodiment of the present disclosure.

FIG. 7A depicts an exemplary pulse signal and its termination, in accordance with one illustrative embodiment of the present disclosure.

FIG. 7B depicts an exemplary pulse signal and its termination, in accordance with one illustrative embodiment of the present disclosure.

FIG. 8A depicts an exemplary pulse signal and its termination, in accordance with one illustrative embodiment of the present disclosure.

FIG. 8B depicts an exemplary pulse signal and its termination, in accordance with one illustrative embodiment of the present disclosure.

Figure 9:
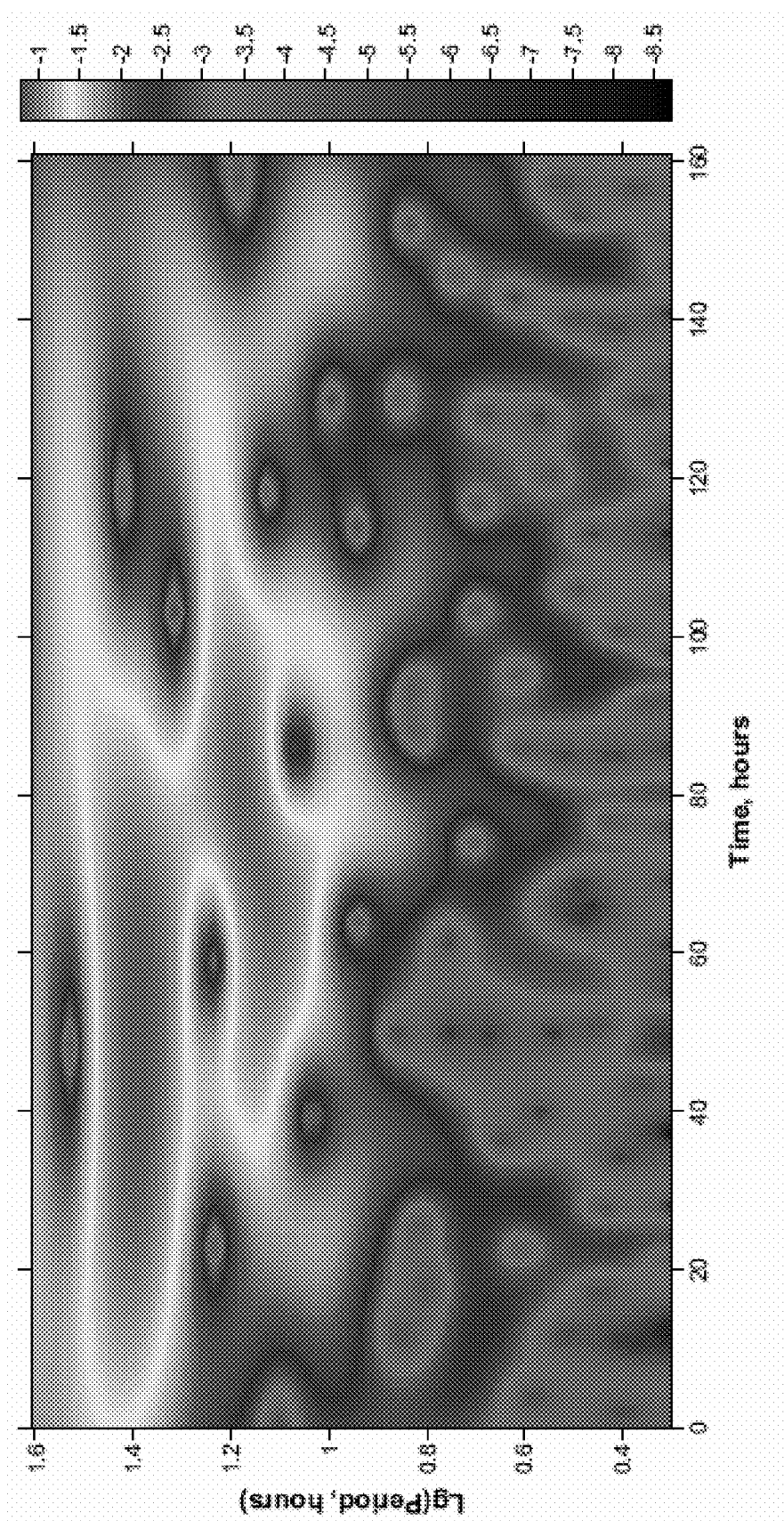

FIG. 9 shows a decimal logarithm of squared Morlet wavelet coefficients of the maximum PFS-variations of 5D clouds over tested cluster numbers from 2 up to 40, after interpolation to uniform 1 h sampling, with two large zones corresponding to periods of approximately 24 hours and 12 hours, in accordance with one illustrative embodiment of the present disclosure.

FIG. 10A depicts an exemplary pulse signal and its termination, in accordance with one illustrative embodiment of the present disclosure.

FIG. 10B depicts an exemplary pulse signal and its termination, in accordance with one illustrative embodiment of the present disclosure.

FIG. 10C depicts an exemplary pulse signal and its termination, in accordance with one illustrative embodiment of the present disclosure.

Figure 11:
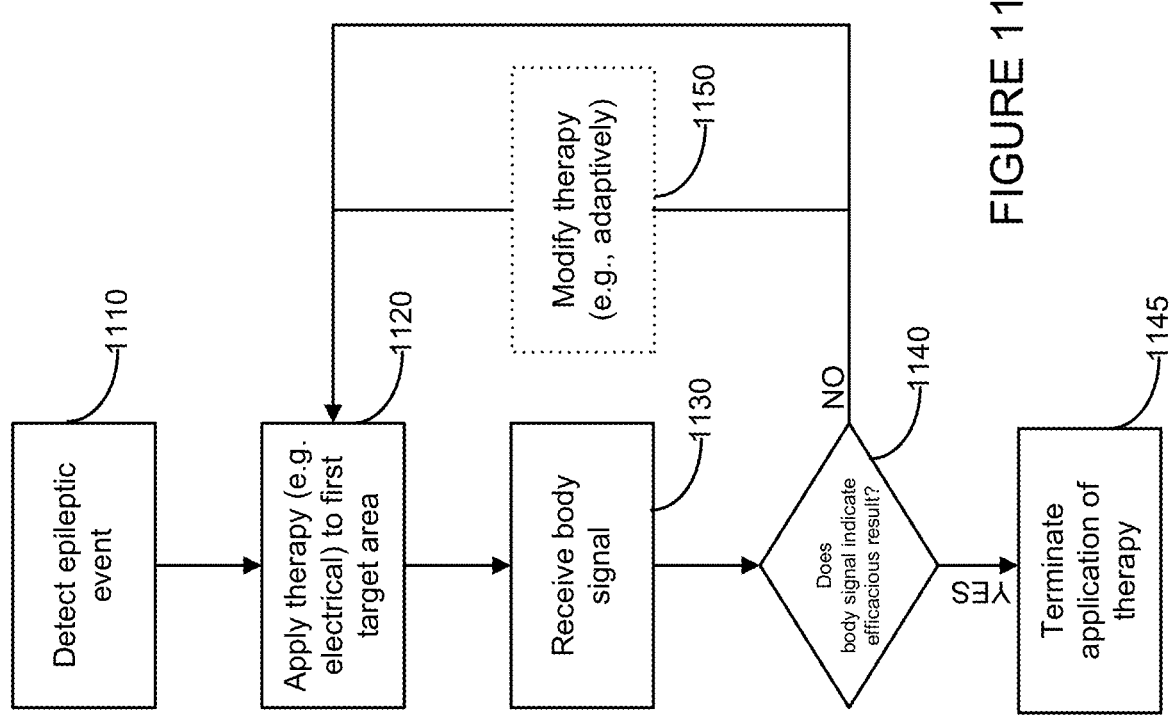

FIG. 11 shows a flowchart depiction of a method, in accordance with one illustrative embodiment of the present disclosure.

Figure 12:
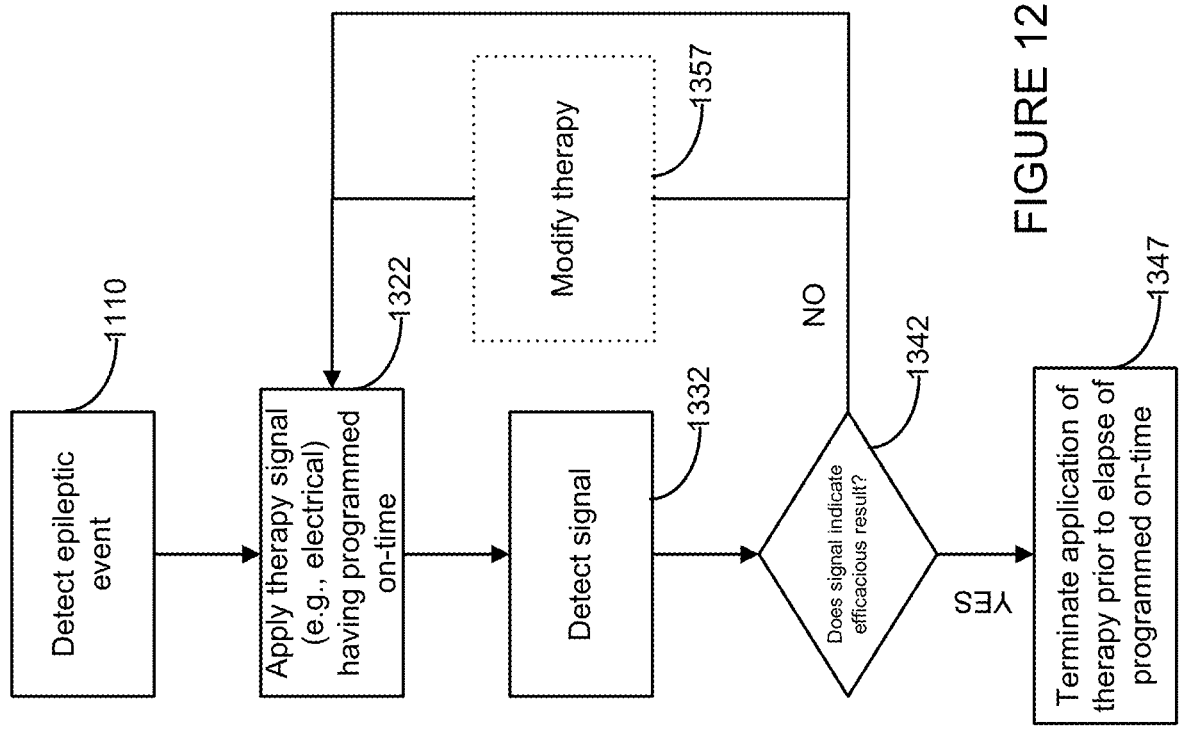

FIG. 12 shows a flowchart depiction of a method, in accordance with one illustrative embodiment of the present disclosure.

DETAILED DESCRIPTION OF THE DISCLOSURE

Embodiments of the present disclosure provide for applying a therapy to a portion of a patient's body and receiving a body signal responsive to the therapy. The body signal responsive to the therapy may be used to determine one or more indications of the efficacy of the therapy. Based upon the efficacy indication(s), the therapy may be terminated, modified or continued. For example, during the application of a therapy that includes a pulsed electrical signal, based upon feedback data relating to efficacy, the therapy may be terminated before the scheduled ending of the signal. Moreover, the signal may be modified to take into account charge-balance considerations due to early termination of the pulse. These considerations may be made for electrical therapies comprising a single pulse, or a plurality of pulses in, e.g., a pulse burst (also referred to as a pulse train). The feedback body signals may include one or more type of signals including, but not limited to, one or more autonomic signals, neurologic signals, metabolic signals, endocrine signals, and/or tissue stress marker signals.

Morphology/phase differences in response to electrical pulses are predictive of a positive (seizure blockage) or negative (no blockage) therapeutic outcome and thus useful as feedback for optimizing a therapy. Several methods exist to compare the shape of waves (without or with suitable transformations) including but not limited to root mean square error and variations of the Dynamic Time Warping such as Fast Dynamic Time Warping, Adaptive Feature Based Dynamic Time Warping, Dynamic Derivative Time Warping, Qualitative Approximation to Dynamic Time Warping. Other measures of distance (i.e., Euclidian, Manhattan, Chebyshev) may be used whenever applicable.

The probability of success in controlling undesirable brain state changes such as seizures depends among other factors on: (a) the quality of spatio-temporal sampling of the signals which, in turn, is based on the type, geometry, and density of electrode arrays and the stability and quality of the electrode-tissue interface (see, e.g., U.S. Pat. No. 7,006,859, which is hereby incorporated herein by reference in its entirety); (b) time and site of delivery of the therapy in relation to the known or predicted onset of undesirable changes; (c) therapy parameter selection (frequency, intensity, waveform shape, etc., in the case of electrical stimulation, or drug type and dose in the case of pharmacological therapy) as a function of space-time dynamics of the pathological process; (d) phase/time of the circadian cycle, when the undesirable changes occur, their intensity, duration and extent of spread; and (e) time elapsed from previous events and their severity (defined as the average of their intensity), duration and extent of spread. Prior art approaches do not take into account these essential considerations that are may be used to optimize control of the undesirable events (e.g., seizures) and prevent loss of function. Such considerations are particularly important for preventing or blocking paroxysmal events such as seizures, cardiac arrhythmias and pain whose behavior is shaped by the substrate in which they occur along with other factors, some of which are stochastic in nature.

Current methods or therapies for preventing, blocking or abating undesirable or abnormal state changes that rely on vehicles or media that must diffuse or travel through tissue (from the source(s) to the target(s) to perform their actions) do not adequately account for delays, uneven diffusion, and, in the case of oscillations/waves, the possibility of formation of intermediate frequencies (heterodyning) or aliasing which, in turn, may result in undesirable (or desirable but uncontrollable) resonances with the frequency at which the neurons or cells (e.g., heart or brain) oscillate.

Delays in diffusion resulting in uneven therapy penetration into target tissue (charge densities in the case of electrical currents, concentrations in the case of drugs/ compounds, or of temperatures in the case of cooling) likely compromise efficacy and are not only the result of the degree of tissue anisotropy from where the state change takes place, but also of the size and macroscopic shape of the tissue. Size and macroscopic shape are important since the abnormal/ undesirable activity also diffuses through tissue with (a) certain speed(s) and direction(s). Improvements provided by embodiments of the present disclosure include: (a) monitoring and controlling, in real time and at the appropriate spatio-temporal scale, the space-time dynamics of a diffusive pathological process through optimization of the space-time dynamics of a diffusive therapy's (current densities, drug concentration or temperature) direction, speed and extent of diffusion and (b) using signals and scales representative of the space-time dynamics of the pathological process as feedback to optimize in real-time (and off-line for some applications) the space-time dynamics of the therapy.

This approach requires that the pathological events' signals or defining features be adequately sampled spatio-temporally, and that timing of delivery, spatial diffusion and other features of the therapy be adjusted/controlled as a function of local and global space-time dynamics including those of the tissue and its components such as neurons, heart cells, brain cells, etc. Since both the abnormal events and the therapies are diffusive processes, spatio-temporal and geometric factors that cause differences in speed, direction, shape and distances between the advancing fronts of, for example, a seizure and those of the therapy, if not detected (or if detected but not timely corrected to avoid either undesirable resonances in the case of currents or inadequate charge density, drug concentrations or temperatures), are likely to lack efficacy or exert a paradoxical effect, enhancing the undesirable event.

Linear and non-linear, parametric and non-parametric, geometric/graphical, statistical and conventional and high order spectral methods exist for measuring, comparing and modeling brain activity that may be used in this disclosure. Also, brain activity may be recorded in multiple domains: electrical, magnetic, thermal, optical, chemical, acoustic, mechanical (e.g. pressure or movement) in any combination of those domains using commercially available sensors, and may be analyzed using myriad available methods in the time or frequency domains. Models of: a) the abnormal neural/ brain activity (without treatment); b) the behavior of the therapy in a controllable virtual medium and c) of the interactions of the abnormal activity and the therapy may be constructed for use in the present disclosure for optimization purposes.

The present disclosure takes into account that therapy delivered to tissue is influenced by the space-time-state tissue dynamics and, in this sense, is a dependent (not an independent) variable to which tools and means for addressing the inherent but manageable limitations may be applied to adapt and optimize the therapy as needed not only for each subject, but also for the region from where the undesirable brain activity originates, the state of the system (e.g. awake vs. asleep), time of day, or other factors contributing to the non-stationarity of brain dynamics. The cytoarchitectonic diversity of the cortical mantle and of subcortical structures may be factored into the strategies for therapy delivery. Location, type, size and number of sensors for signal analyses and of therapy sources and type(s), are also important for prevention, blockage or abatement of seizures, cardiac arrhythmias or pain. In some embodiments, the disclosure herein includes the ability to track/measure tissue resistivity, osmolality and tissue responses, among other variables, and use latencies, amplitudes, waveforms/types and actual frequencies and periods of the responses to create maps as a function of time and state that are used to adjust therapies automatically or manually to improve safety, efficacy, and/or tolerability. Measurements of resistivity, osmolality, diffusivity, temperature, ionic and neurotransmitter concentrations, pressure/strain, motility, acoustic activity and of responses to electrical, chemical, physiological (e.g., visual), cognitive and affective stimulation may be performed with commercially available sensors, and may be used to determine whether a therapy has an efficacious effect on the course of the seizure. Specific mention is made of measuring cognitive functions, which are among the most meaningful indices of therapeutic efficacy (especially in the case of partial complex or generalized seizures), and of using these measures to adapt and optimize therapies.

Embodiments of the present disclosure may overcome the limitations of the prior art by: (a) quantifying and characterizing in real-time (and, when advantageous, off-line) the electrical, chemical, thermal, mechanical, acoustic and cognitive (for brain) behavior of biological tissues at one or more spatial scales using passive and/or active probes; (b) recording with precision and high fidelity not only the conventionally measured EEG frequencies (0.1-100 Hz) but also ultra-slow (e.g., 0.001 Hz) and ultra-fast (>500 Hz) brain wave oscillations; (c) using this information to determine (and adapt and update as needed) the type, timing, and/or location of therapy delivery, geometry and number of therapy sources, duration and frequency/rate of therapy delivery. Advantageously, embodiments of the disclosure may, as a priority goal, prevent the event (e.g., a seizure) from occurring. In other embodiments, where prevention is not possible the disclosure may facilitate blocking or terminating the event after it occurs but before the subject is impaired. Where blocking or termination is unsuccessful, the disclosure may allow therapies that lessen severity of the event, so as to minimize dysfunction. In some embodiments, the disclosure may include delivering a warning to the patient or a caregiver if prevention fails, and systems of the disclosure may involve logging to memory all relevant data about the spatio-temporal behavior of the brain activity and of the therapy.

Both sensors and therapy sources of the present disclosure may be multimodal (e.g., electrical, optical, chemical, pressure, thermal, acoustic, etc.). Their number location, functions, and status (active or dormant) may vary according to the task at hand.

Neurostimulation proposals have focused on providing a responsive therapy, and/or implementing safety precautions (e.g., providing warnings to the patient or caregivers, or summoning emergency assistance). Such interventions, however, have failed to address the subsequent problem of determining when the patient's condition has recovered and/or improved such that implemented safety precautions may be disabled, and the patient's control over his/her environment may be restored. This issue is important because of the inherent lack of temporal correlations between termination of an acute medical condition (e.g., the abnormal brain electrical activity of a seizure) and termination of the medical sequelae associated with the acute condition (e.g., the end of cognitive dysfunction associated with a post-ictal state, and resumption of an inter-ictal state).

Appropriate interventional strategies must consider the fact that the appearance of body signals (e.g., ECoG, EKG) indicative of seizures may precede behavioral impairment or other pathological changes (e.g., cardio-respiratory or metabolic abnormalities, among others) that may increase the risk of injury and of other co-morbidities. Additionally, the recovery of behavioral functions and resolution of abnormalities caused by seizures commonly lags behind (by seconds to hours to days) the spontaneous or induced (e.g. resulting from treatment) termination of the abnormal body signal (e.g., ECoG) used for detection of seizures. Accordingly, comprehensive determination of therapeutic efficacy requires the analysis of multiple body signals. These analyses must be performed at multiple time scales that reflect the "time constants" or rates at which each body signal changes from the non-seizure to the seizure state and vice-versa.

Thus, although a therapy may have been efficacious in terminating a seizure as measured using one or more body signals (e.g., ECoG, which possibly has the fastest rate of change and is highly reliable), this outcome cannot be generalized to other body signals. For example, termination of tonic-clonic activity, which in the appropriate context is indicative of therapeutic efficacy, is not necessarily associated with an immediate or simultaneous recovery of other body signals, such as consciousness and cognitive functions, tachycardia, or metabolic acidosis. Consequently, automatic disabling of a warning signal indicative of cognitive impairment following the termination of tonic-clonic activity and/ or enabling operation of a vehicle based on a single efficacy measure would, in most cases, be unwarranted and unsafe, especially if this signal has a fast rate of recovery as compared to the rate of recovery of other relevant body signal. Embodiments of the present disclosure take into account the clinical impact or consequences of the inherent differences in the rate of change and recovery to baseline or to interictal values (from ictal values) of the various body signals (e.g., neurologic, autonomic, metabolic, endocrine, tissue stress markers, or physical fitness/body integrity) to automatically implement a safe and clinically beneficial plan for patients with epilepsy.

In one embodiment, a warning may be automatically issued with a seizure detection and the warning may be subject to modification, termination or reissuance based on the response to therapy of at least two body signals. For example, ECoG, EKG, and complex reaction time responses may be used to detect tonic-clonic seizures and to determine the efficacy of a therapy. The cessation of epileptiform activity in the ECoG, which would be the first expected change due to its fast rate (e.g., on a "microscopic" scale), may lead to immediate termination of therapy delivery, but not of the warning, which may be downgraded (e.g., if a color scale is used, from red to orange) in light of the ECoG's beneficial response. Monitoring of EKG may reveal that a tachycardia (exemplary peak rate: 150 beats/min) associated with the seizure resolves (exemplary heart rate: 80 beats/min) sometime (e.g., 310 sec) after termination of epileptiform activity in the ECoG. The EKG change may result in a second downgrade of an alarm status (from orange to yellow) but not termination of the warning altogether. The improvement in ECoG and heart rate may trigger, in this example, re-administration of a complex reaction time test. If the patient passes the test, the warning may be cancelled, and if not it remains in place, and the reaction time test may be re-administered, based either on recovery to baseline of some other body signal (e.g., a metabolic signal) or a pre-programmed time interval. Return of the values or characteristics of these three body signals—which have different relevant time scales—to interictal levels may cause the automatic re-enabling of a motor vehicle, an appliance, a power tool, etc. that may have been disabled upon detection of the seizure.

As a further example, if the patient in the preceding example had never had EKG abnormalities (e.g., ST segment depression) during seizures, but such a change occurred in the latest seizure after the warning had been twice downgraded (e.g., after ECoG and tachycardia had disappeared), the emergence of the EKG morphology change could automatically trigger an upgrade of the warning (to red in this example) and/or implementation of therapeutic or other measures.

The examples above are but two of myriad ones that will be the subject of embodiments and implementations in this disclosure.

Turning now to FIG. 1A, a stylized medical device system is depicted. The medical device system comprises a medical device (MD) 200 and at least one sensor 212.

In some embodiments, the medical device 200 may be implantable, while in other embodiments, such as that shown in FIG. 1A, the MD 200 may be completely external to the body of the patient.

The sensor 212 may be implanted in the patient's body, worn external to the patient's body, or positioned in proximity to but not in contact with the patient's body. The sensor 212 may be configured to receive cardiac activity data, body movement data, responsiveness data, awareness data, respiratory data, blood pressure data, or other data from the patient's body.

FIG. 1A depicts the medical device (MD) 200 being in wireless communication 211 with the at least one sensor 212. In other embodiments (not shown), the MD 200 may be in communication with the at least one sensor 212 via a lead or other wired communication channel.

The medical device system shown in FIG. 1A also includes at least one electrode 282. In the depicted embodiment, the electrode 282 may be implanted in the patient's brain 105 such that the terminus of the electrode 282 may be in proximity to a brain region 110 which may be an epileptogenic focus (depicted by a star in FIG. 1A) of the patient.

Not shown in FIG. 1A is an alternative embodiment, wherein a plurality of leads 282 may be implanted in the patient's brain 105. A plurality of leads 282 may be implanted such that their termini may all be in proximity to a single brain region. Alternatively, the plurality of leads 282 may be implanted such that their termini are in proximity to a plurality of different brain regions. For example, if the patient has multiple epileptogenic foci, a plurality of leads may be implanted such that each epileptogenic focus may have at least one lead terminus in proximity thereto.

Also, FIG. 1A depicts the MD 200 being in wireless communication 281 with the at least one electrode 282. In other embodiments (not shown), the MD 200 may be in communication with the at least one electrode 282 via a lead or other wired communication channel.

Figure 1B:
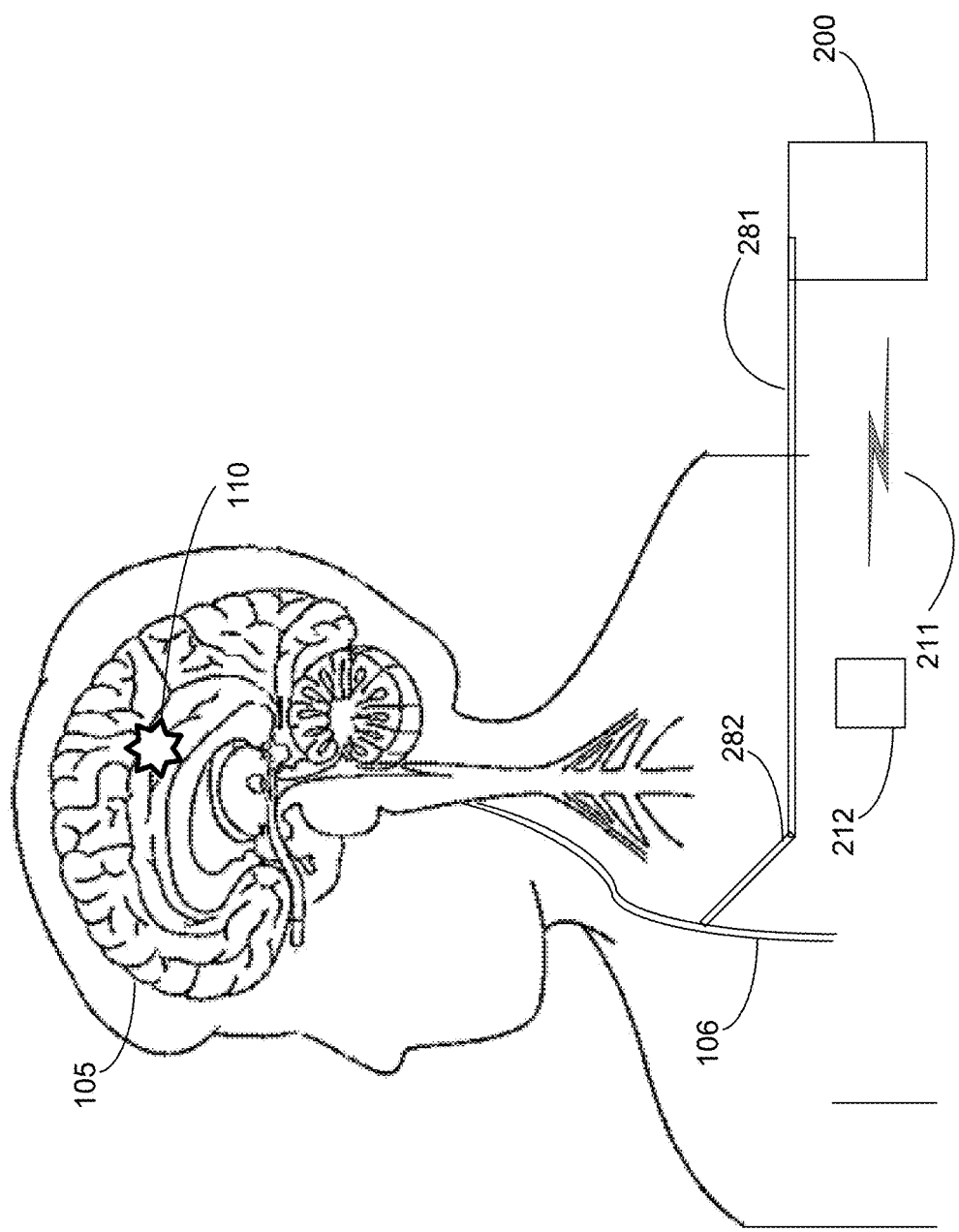
FIG. 1B depicts a medical device system, comprising an electrode implanted in proximity to a vagus nerve of a patient, in accordance with one illustrative embodiment of the present disclosure.

FIG. 1B depicts a stylized medical device system according to another embodiment of the present disclosure. In this embodiment, an electrode 282 is implanted such that its terminus is in proximity to a cranial nerve, such as vagus nerve 106. The electrode 282, shown in wired communication with the MD 200 via lead 281, may be used to deliver an electrical stimulation therapy to the vagus nerve 106 for treatment of an epileptic event.

FIG. 2 presents a block diagram of a medical device system, in accordance with one illustrative embodiment of the present disclosure.

The MD 200 may comprise a controller 210 capable of controlling various aspects of the operation of the MD 200. The controller 210 may be capable of receiving internal data or external data, and in one embodiment, may be capable of causing a therapy module 275 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 may be capable of affecting substantially all functions of the MD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a various data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

In other embodiments, one or more electrode(s) 282 may be adapted to be coupled to at least one neural structure of a patient. The neural structure may be one or more of a target area of the brain region of the patient, a target area of a cranial nerve of a patient, a target area of the spinal cord of a patient, a target area of a sympathetic nerve structure of the patient, a target area of a peripheral nerve of the patient, a target area of a nerve root of a patient, a target area of a cardiovascular neural structures such as a baroreceptors or neural structures in the heart such as a sinoatrial node or an atrioventricular node, sensory receptors of a patient, proprioceptives receptor of a patient, or a target area of a skin receptor of a patient.

The MD 200 may also comprise a power supply 230. The power supply 230 may comprise a battery, voltage regulators, capacitors, etc., to provide power for the operation of the MD 200, including delivering a therapeutic electrical signal. The power supply 230 comprises a power source that in some embodiments may be rechargeable. In other embodiments, a non-rechargeable power source may be used. The power supply 230 provides power for the operation of the MD 200, including electronic operations, such as sensing functions, and therapeutic electrical signal generation, delivery, modification and termination functions. The power supply 230 may comprise a lithium/thionyl chloride cell or a lithium/carbon monofluoride (LiCFx) cell if the MD 200 is implantable, or may comprise conventional watch or 9V batteries for external (i.e., non-implantable) embodiments. Other battery types known in the art of medical devices may also be used.

The MD 200 may also comprise a communication unit 260 capable of facilitating communications between the MD 200 and various devices in a device system. In particular, the communication unit 260 may be capable of providing transmission and reception of electronic signals to and from a monitoring unit 270, such as a handheld computer or PDA that can communicate with the MD 200 wirelessly or by cable. The communication unit 260 may include hardware, software, firmware, or any combination thereof.

The MD 200 may also comprise one or more sensor(s) 212 coupled via sensor lead(s) 211 to the MD 200. Sensor(s) 212 are capable of detecting one or more body signals from a patient's body. Exemplary body signals include, but are not limited to, those related to an autonomic index, such as the patient's heart beat, blood pressure, and/or temperature, among others; signals related to a neurologic index, signals related to a metabolic index, signals related to an endocrine index, and signals related to a tissue stress marker index. For example, the body signals may be at least one of cardiac signals, body movement signals, or brain electrical activity signals from the patient's body.

In one embodiment, the sensor(s) 212 may be the same as electrode(s) 282 for delivering electrical therapy to a target tissue. In other embodiments, the sensor(s) 212 are separate structures that may be placed on the patient's skin, such as over the patient's heart or elsewhere on the patient's torso for sensing heart beats. The sensor(s) 212 and accompanying leads may be considered an interface for the MD 200 to receive at least one of autonomic data, neurologic data, metabolic data, endocrine data, stress marker data, or other data.

More information on body signals, such as cardiac signals, respiratory signals, body movement signals, skin resistance signals, responsiveness signals, and awareness signals, as well as techniques and devices for the acquisition thereof and the determination of autonomic indices, neurologic indices, metabolic indices, endocrine indices, and stress marker indices, is provided by U.S. patent application Ser. No. 12/896,525, filed Oct. 1, 2010, which is incorporated herein by reference in its entirety.

In one particular embodiment, the sensor(s) 212 may be configured to collect at least one of cardiac signals, body movement signals, cognitive signals, or brain electrical activity signals from the patient's body.

The MD may also comprise an epileptic event detection module 265. The epileptic event detection module 265 may be configured to detect an epileptic event (e.g., a seizure onset, a seizure effect, a seizure end) from any desired input suitable for doing so. For example, in one embodiment, the epileptic event detection module 265 may be configured to detect an epileptic event from brain electrical activity data, e.g., EEG data. In another embodiment, the epileptic event detection module 265 may be configured to detect an epileptic event based on other body signal(s). In one particular embodiment, the epileptic event detection module 265 may be configured to detect an epileptic event based on at least one of a cardiac activity indicative of an epileptic event (e.g., changes in a heart rate, rate of change or heart rate, or other changes in the patient's ECG signal) or a motor activity indicative of an epileptic event (e.g., a kinetic signal indicative of patient body movement (or lack thereof) in one or more body areas from a sensor such as a triaxial accelerometer).

More information regarding detection of epileptic events from sensed body signals, and determination of severity of and body locations affected by epileptic events, can be found in U.S. patent application Ser. No. 12/756,065, filed Apr. 7, 2010; U.S. patent application Ser. No. 12/770,562, filed Apr. 29, 2010; U.S. patent application Ser. No. 12/896,525, filed Oct. 1, 2010; U.S. patent application Ser. No. 13/040,996, filed Mar. 4, 2011; U.S. patent application Ser. No. 13/091, 033, filed Apr. 20, 2011; and U.S. patent application Ser. No. 13/098,262, filed Apr. 29, 2011; all of which are hereby incorporated herein by reference in their entirety.

In one embodiment, the MD 200 may also comprise a therapy module 275 capable of generating and delivering a therapy in response to an indication that a seizure has been detected by epileptic event detection module 265. The therapy may include one or more of a number of therapy modalities, such as an electrical therapy delivered to one or more electrodes 282 via one or more leads 281. Electrodes 282 may be configured for coupling to one or more neural structures of a patient (e.g., a brain structure and/or a cranial nerve). Therapy may be delivered to the electrode(s) 282 by the therapy module 275 based upon instructions from the controller 210.

Therapy module 275 may comprise various circuitry, such as electrical signal generators, impedance control circuitry to control the lead impedance, and other circuitry that receives instructions relating to the delivery of the electrical signal to tissue. The therapy module 275 may be capable of delivering an electrical therapy over the leads 281 to the electrode(s) 282. The therapy module 275 may be configured to apply an electrical therapy, which may comprise one or more stimulation pulses, to at least one neural structure of the patient based on an indication of an epileptic event.

The electrical therapy, and/or each stimulation pulse thereof, may comprise a plurality of programmable parameters defining or relating to the therapy, such as pulse width, current amplitude, pulse frequency, voltage amplitude, pulse waveform, pulse burst duration, total number of pulses, number of pulses per unit time, inter-pulse interval, pulse phase, number of phases in a pulse, number of phases in a pulse burst, polarity of pulse phase, current density per pulse, and a total current density for a pulse burst. In addition, a number of parameters may be determined that are related to the interaction of the signal and the body of the patient, and which may also be used to apply the therapy signal at a particular time, such as a degree of isotropy of current flow, a time delay between the delivery of a current and its arrival at a body target, a timing of therapy delivery (e.g., relative to a zero-crossing, an extremum, or a region of ascending or descending slope of the body signal(s) used to determine efficacy).

In one embodiment, the electrical therapy may have a programmed therapy duration that may be terminated prior to the elapse of the programmed duration, in response to an indication of an efficacious effect of the therapy.

In one embodiment, the electrical therapy has a short duration compared to existing stimulation therapies, and may be as short as 5 seconds, 1 second, 500 milliseconds, 250 milliseconds, 100 milliseconds, 50 milliseconds, 20 milliseconds, or even less.

In one embodiment, the therapy module 275 may determine a timing of the therapy relative to the detection of the epileptic event by detection module 265. For some seizures, the therapy module may determine that the therapy should be applied immediately upon detection of the epileptic event by detection module 265, while for other seizures therapy module 275 may determine that the therapy should be applied at a time after the detection of the seizure. This may involve assessment of one or more body parameters to determine when the therapy is likely to be effective. If the therapy module 275 determines, at the time of detection of a seizure by detection module 265, that the therapy module is not likely to be effective based on one or more body parameters, the therapy module may impose a delay period before applying the therapy to the patient. The therapy may be a fixed delay period, after elapse of which the therapy is applied with no further assessment, or may involve a variable delay in which the therapy is not applied until one or more body parameters indicate that the therapy is likely to be effective (or is not likely to be ineffective).

Various therapy modalities may be delivered to target tissue of the subject in response to a detection of an epilepsy event. In one embodiment, the delivered therapy may comprise one or more of an electrical therapy, a magnetic therapy, a chemical therapy, a heating or cooling therapy, applying a positive or negative pressure to a target tissue, an optical therapy, a cognitive therapy, a sensory therapy, or a motor therapy.

In one embodiment, the MD 200 may also comprise a responsive action module 276 capable of implementing one or more actions other than delivering a therapy, in response to an indication that a seizure has been detected by epileptic event detection module 265. The actions may be at least one of logging a time of the epileptic event, logging the duration of the epileptic event, logging the severity of the epileptic event, logging the type of therapy, logging the effects of the therapy (e.g., beneficial, detrimental, or no effect), if any, delivered to treat the epileptic event, warning the patient, a caregiver, or a medical professional of the epileptic event, canceling such a warning, or modifying such a warning, among other actions.

The MD 200 may also comprise an efficacy determination module 266. The efficacy determination module 266 may be configured to receive collected body signal(s) from the sensor(s) 212, and determine whether a therapy applied by the therapy module 275 to treat an epileptic event has an efficacious effect on the detected event. These effects may involve a continuum ranging from small effects (e.g., a therapy that slightly reduces the severity of a seizure or slows the rate of its spread to other brain or body areas), to major efficacious effects (e.g., rapidly or immediately terminating a seizure). Moreover, efficacious effects may be identified and quantified or determined by one or more efficacy indices, and may be compared to one or more thresholds of efficacy in determining whether a therapy has provided an adequate beneficial effect.

In one embodiment, the efficacious effect may be a return of an efficacy index, such as a cardiac index, towards an interictal baseline in response to a therapy initiated after detection of an epileptic event. A "cardiac index" refer to any value that can be calculated from a cardiac signal at one or more timescales ranging from microscopic, mesoscopic, or macroscopic. Exemplary cardiac indices include, but are not limited to, heart rate (HR), a first derivative thereof, a second derivative thereof, a heart rate variability (HRV), a first derivative thereof, a second derivative thereof, or an EKG morphology index (e.g., a time between any two of the P, Q, R, S, and T waves of the EKG complex, an amplitude, shape or feature of any one or more of the P, Q, R, S, and T waves, or a ratio of the amplitude of any two or more of the P, Q, R, S, and T waves), among others. In another embodiment, the efficacious effect may be termination or amelioration of the epileptic event (e.g., detecting an end of a seizure after initiating a therapy). In another embodiment, the efficacious effect may be a return of a cognitive function towards an interictal baseline.

For example, in a seizure characterized by an increase in a short-term HR measure (e.g., a median HR in a 5-second or 5 beat moving window), efficacious effects may include reversing a measured HR increase (i.e., lowering HR), halting a HR increase (i.e., maintaining HR at a single level that may be less than a typical seizure maximum HR), slowing the rate at which HR is increasing (i.e., reducing a short-term slope measure of FIR), or multiple effects (e.g., slowing HR followed by reversal of HR). In another example, in a seizure characterized by clonic movements detected using a triaxial accelerometer, efficacious effects may include cessation of the clonic movements, or a reduction in their amplitude, force, acceleration or velocity.

There are intra- and inter-class differences in the rate (and magnitude) of changes of autonomic, neurologic, endocrine metabolic and tissue stress marker indices during seizures, and also in the rate at which they recover after the spontaneous or induced (e.g., therapy) termination of seizures. The rate of change of cortical electrical activity characteristic of seizures is possibly the fastest among all indices, allowing rapid assessment of efficacy of a therapy. Cardiac changes are not as rapid as brain electrical activity changes, but cardiac activity is adequate for rapid assessment of efficacy (or lack thereof). For example, changes in R-R intervals (which requires only two heart beats for calculation) may be used to assess efficacy. In a particular example, if the mean ictal R-R interval in a patient is 0.46 s (range 0.42-51 s), an increase to 0.62 s after delivery of therapy may be used an indication of a beneficial effect (indicating that the heart has slowed down). Efficacy indices can be absolute or relative, and may or may not be normalized.

The efficacy index may be a +/−[0,1] function. Alternatively or in addition, the efficacy index may be assessed using temporal or spatial criteria for neuronal oscillations corresponding to an epileptic event. Alternatively or in addition, the efficacy index may be assessed using at least one of a magnitude of a change in a value of an autonomic index, a magnitude of a change in a value of a neurologic index, a magnitude of a change in a value of a metabolic index, a magnitude of a change in a value of an endocrine index, or a magnitude of a change in a value of a stress marker index. The value may be an absolute or relative value. Alternatively or in addition, the value may be a derivative of the at least one index referred to above. For example, if the mean value of the slope of HR during seizures is 0.6 (range: 0.56-0.63) and it is reduced to 0.15 (indicating a reduction of the rate at which HR is increasing), immediately after which it becomes negative (indicating slowing of the heart), efficacy is shown.

In another embodiment, an efficacious effect may be determined from a change in at least one of an amplitude variance, an extrema variance, a zero-crossing variance or a slope variance of a body index, wherein the change is temporally correlated with applying the therapy. Large changes in EEG/ECoG amplitude or frequency variance characterize seizures; a sudden, large drop (or lack thereof) in this signal variance during or after delivery of therapy may be used to determining efficacy or lack thereof.

The efficacy index may comprise information from one or more indices, one or more timescales, and/or one or more other parameters. In a preferred embodiment, the efficacy index comprises a short-term measure of efficacy relating to a mesoscopic timescale or a microscopic timescale.

The terms "microscopic," "mesoscopic," and "macroscopic" may be used herein to refer to various scales of observation, as follows. "Microscopic" may correspond to a scale of observation of less than 10 seconds, such as less than 5 seconds, less than 4 seconds, less than 3 seconds, less than 2 seconds, less than 1 second, less than 500 milliseconds, less than 250 milliseconds, less than 100 milliseconds, or less than 50 milliseconds.

"Mesoscopic" may correspond to a scale of observation from 10 seconds to 300 seconds, such as from 20 seconds to 300 seconds, from 30 seconds to 300 seconds, from 60 seconds to 300 seconds, from 90 seconds to 300 seconds, from 120 seconds to 300 seconds, from 180 seconds to 300 seconds, from 240 seconds to 300 seconds, from 10 seconds to 240 seconds, from 10 seconds to 180 seconds, from 10 seconds to 120 seconds, from 10 seconds to 90 seconds, from 10 seconds to 60 seconds, from 10 seconds to 30 seconds, or from 10 seconds to 20 seconds.

"Macroscopic" may correspond to a scale of observation longer than 300 seconds, such as longer than 10 minutes, longer than 30 minutes, longer than 1 hour, longer than 8 hours, longer than 1 day, longer than 1 week, longer than 1 month, longer than 3 months or one season, or longer than 1 year. Macroscopic scales of observation longer than 1 month may be termed "megascopic."

In one embodiment, the efficacy index comprises at least one of a temporal component (e.g., an epileptic event duration), a spatial component (e.g., an extent of spread of an epileptic event), a cognitive component (e.g., an extent of loss of awareness and/or responsiveness by the patient during the epileptic event), or a motor activity component (e.g., an extent of abnormal motor activity in the patient's body during the epileptic event). The spatial component may be determined by comparing a pattern of seizure spread to a reference pattern of seizure spread. The pattern of seizure spread may comprise a plurality of feedback body signals affected by the epileptic event.

The efficacy index may be based upon a change in a number of body signals affected by the therapy. "Affected by" in this context means the number of signals from which a body index or indices can be calculated, wherein the body index or indices indicates an efficacious effect (or a lack of an efficacious effect, and/or an adverse effect).

In one embodiment, an efficacious effect can be determined from an attenuation of at least one component of a seizure below a reference value.

In another embodiment, an efficacious effect may be considered to be an improvement of the epileptic event, or a termination of the epileptic event. Conversely, an adverse effect may be considered to be a worsening of the epileptic event. "Worsening" and "improvement" can be defined as increases or decreases, respectively, in severity of the epileptic event, for example as changes in an efficacy index or an index used for detecting the epileptic event. Both a lack of beneficial change in the epileptic event and a worsening of the epileptic event can be considered as lack of an efficacious effect, non-efficacious effects, or comparable terms.

An efficacious effect may be determined using any of a number of body signals and/or techniques. In one embodiment, a determination of an efficacious effect may be based on a non-neural body signal, and in a particular embodiment, at least one of a cardiac activity indicative of a response to an epileptic event or a motor movement indicative of a response to an epileptic event. In one embodiment a determination of an effect may be based on techniques such as calculation of the change in mean, median, SD or variance using time-based, frequency-based, fractal or variability analyses methods. In one embodiment, a determination of an efficacious effect may be determined by an improvement in an index used to detect the epileptic event itself, (e.g., an improvement in a ratio of a short-term heart rate and a long-term heart rate, or the cessation of an epileptic movement as determined by a triaxial accelerometer).

The MD 200 may also comprise a therapy modification module 285. The therapy modification module 285 may be configured to modify at least one parameter of an electrical stimulation pulse, based on an indication the therapy did not have an efficacious effect. In embodiments wherein the MD 200 includes a therapy modification module 285, the therapy module 275 may be configured to apply the modified therapy to at least one neural structure.

Therapy modification unit 285 may receive data from the efficacy determination module 266 relating to the efficacy resulting from the therapy delivered by the MD 200. Therapy modification unit 285 may determine that the present therapy should be modified, but not terminated. The modification may include modifying one or more parameters defining the or relating to the therapy, as discussed above in reference to therapy module 275.

Accordingly, once an indication of efficacy relating to the therapy has been received and processed, the therapy modification unit 285 may determine that it may be beneficial to modify the therapy. In some embodiments, this may include modifying the therapy prior to the elapsed duration of a therapy having a programmed duration. The modification may comprise increasing one or more parameters defining the therapy, decreasing one or more parameters, or both increasing and decreasing at least one parameter defining the therapy. This may correspond to increasing the strength of the signal, decreasing the strength of the signal, or altering the timing of the signal.

In one embodiment, therapy modification unit 285 may include modifying the timing of applying a therapy from therapy module 275 to the patient.

The MD 200 may also comprise a therapy termination module 295. The therapy termination module 295 may be configured to terminate a therapy, based on an indication the therapy may have an efficacious effect. The therapy termination module 295 may also be configured to terminate therapy after a safety duration, e.g., after a predetermined amount of therapy has been applied without an efficacious effect. The therapy termination module 295 may also be configured to terminate therapy if an adverse or intolerable effect is detected. Therapy termination to avoid overstimulation may be advisable where the epileptic event may be intractable to therapy, to preserve MD 200 battery life and/or minimize harm potentially caused by the therapy including but not limited to re-initiating the seizure.

The therapy termination module 295 may also be configured to terminate a therapy in response to a determination that a time period for the application has exceeded a reference time period, a current density for the application has exceeded a reference current density value, the application has been performed a predetermined number of times, or an adverse effects is likely to occur, is occurring, or has occurred.

In another embodiment, therapy may be continued without modification if the epileptic event is improved but is not terminated.

In many instances, the therapy may provide an efficacious effect. In some embodiments, the present disclosure terminates therapy upon determination of an efficacious effect. Terminating therapy based on an indication the therapy may have an efficacious effect may mean that further stimulation is not necessary. In some situations further stimulation may be deleterious, and may "rekindle" or re-start an epileptic event after the therapy was efficacious against the epileptic event originally detected. Without being bound by theory, it is believed that many epileptic seizures may be responsive to therapy early in the course of the seizure, but may be re-initiated because therapy is continued beyond the time at which the seizure is interrupted. Some embodiments of the present disclosure provide improved therapies for treatment of epileptic events by terminating therapy when an efficacious effect is identified, avoiding such seizure "re-kindling".

The therapy termination module 295 may terminate therapy at any time after detection of the epileptic event. In one embodiment, the therapy termination module 295 may terminate therapy within milliseconds of detecting the epileptic event. In one embodiment, the therapy termination module 295 may terminate the therapy within seconds of detecting the epileptic event. The time within which the therapy may be terminated may depend upon factors such as the time required for a therapy to achieve an efficacious effect, the time required for the efficacious effect to be detected and/or identified in a monitored body signal or the time required to detect an adverse and/or an intolerable effect.

The MD system of FIG. 2 may also comprise a body data collection module 287. The body data collection module 287 may be configured to receive one or more body signals, such as signals collected by sensor(s) 212, and perform various processing techniques thereon to provide body data suitable for use in calculations performed by one or more of the epileptic event detection module 265 or the efficacy determination module 266, among others.

The MD system of FIG. 2 may also comprise a monitoring unit 270, which may be a device capable of transmitting and receiving data to and from the MD 200. In one embodiment, the monitoring unit 270 may be a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the MD 200 than another monitoring unit 270 controlled by a healthcare provider. Whether controlled by the patient or by a healthcare provider, the monitoring unit 270 may be a computer, preferably a handheld computer or PDA, but may alternatively comprise any other device that may be capable of electronic communications and programming, e.g., handheld computer system, a desktop computer system, a laptop computer system, a server, a personal digital assistant (PDA), a cellular telephone, etc. The monitoring unit 270 may download various parameters and program software into the MD 200 for programming the operation of the MD, and may also receive and upload various status conditions and other data from the MD 200. Communications between the monitoring unit 270 and the communication unit 260 in the MD 200 may occur via a wireless or other type of communication, represented generally by line 277 in FIG. 2.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, seizure severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting references for one or more detection parameters) using the monitoring unit 270, which may include obtaining and/or analyzing data from the MD 200 and/or data from the database unit 250 and/or the local database unit 255.

One or more of the blocks illustrated in the block diagram of the MD 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC, etc.

Turning now to FIG. 3A, a block diagram depiction of an MD 200 is provided, in accordance with one illustrative embodiment of the present disclosure. In the depicted embodiment, the MD 200 may comprise a body data collection module 287. Body data collected by the body data collection module 287 may provide sufficient information to the therapy modification unit 285 and/or to the therapy termination unit 295 such that the MD 200 can terminate or modify the therapy being delivered.

FIG. 3A depicts an exemplary implementation of the body data collection module 287 described in FIG. 2. The body data collection module 287 may include hardware (e.g., amplifiers, accelerometers), tools for chemical assays, optical measuring tools, a body data memory 350 for storing and/or buffering data in the body data collection module 287. The body data memory 350 may, in some embodiments, be adapted to store body data for logging or reporting purposes and/or for future body data processing and/or statistical analyses. The body data collection module 287 may also include one or more body data interfaces 310 to provide an interface for input/output (I/O) communications between the body data collection module 287 and body data units/modules (e.g., [360-370], [373-376]) via connection 380. Connection 380 may be a wired or wireless connection, or a combination of the two. The connection 380 may be a bus-like implementation or may include an individual connection (not shown) for each, or some number, of the body data units (e.g., [360-370], [373-376]). The connection 380 may also include connection elements.

In various embodiments, the body data units may include, but are not limited to, an autonomic data acquisition unit 360, a neurologic data acquisition unit 370, an endocrine data acquisition unit 373, a metabolic data acquisition unit 374, a tissue stress marker data acquisition unit 375, a quality of life (QOL) unit 274 (not shown), and/or a physical fitness/integrity acquisition and determination unit 376. In one embodiment, the autonomic data acquisition unit 360 may include a heart beat data acquisition unit 361 adapted to acquire a phonocardiogram (PKG), EKG, echocardiography, apexcardiography and/or the like, a blood pressure acquisition unit 363, a respiration acquisition unit 364, a blood gases acquisition unit 365, and/or the like. In one embodiment, the neurologic data acquisition unit 370 may contain a kinetic unit 366 that may comprise an accelerometer unit 367, an inclinometer unit 368, and/or the like; the neurologic data acquisition unit 370 may also contain a responsiveness/awareness unit 369 that may be used to determine a patient's responsiveness to testing/stimuli and/or a patient's awareness of their surroundings; and the physical fitness determination unit 376 may comprise a body injury logging unit 376b configured to log information relating to body injuries due to epileptic events. These lists are not exclusive, and the body data collection module 287 may collect additional data not listed herein, that would become apparent to one of skill in the art having the benefit of this disclosure. The body data units ([360-370], [373-376]) may be adapted to collect, acquire, receive/transmit heart beat data, EKG, PKG, echocardiogram, apexcardiogram, blood pressure, respirations, blood gases, body acceleration data, body inclination data, EEG/ECoG, and/or the like.

The body data interface(s) 310 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for signals such as those to/from any of the body data units/modules (e.g., ([360-370], [373-376])) or signals to/from other units/modules of the MD 200. The A/D converter(s) 330 may be adapted to convert analog input signals from the body data unit(s)/module(s) into a digital signal format for processing by controller 210 (and/or processor 215). A converted signal may also be stored in a buffer(s) 340, a body data memory 350, or some other memory internal to the MD 200 (e.g., memory 217, FIG. 2) or external to the MD 200 (e.g., monitoring unit 270, local database unit 255, database unit 250, remote device 292). The buffer(s) 340 may be adapted to buffer and/or store signals received by the body data collection module 287 as well as signals to be transmitted by the body data collection module 287. In various embodiments, the buffer(s) 340 may also be adapted to buffer and/or store signals in the body data collection module 287 as these signals are transmitted between components of the body data collection module 287.

As an illustrative example, in one embodiment, data related to a patient's respiration may be acquired by respiration unit 364 and sent to the MD 200. The body data collection module 287 in the MD 200 may receive the respiration data using body data interface(s) 310. As the data is received by the body data interface(s) 310, the incoming data may be amplified/conditioned by amplifier(s) 320 and then converted by A/D converter(s) into a digital form. The digital signal may be buffered by a buffer(s) 340 before the data signal is transmitted to other components of the body data collection module 287 (e.g., body data memory 350) or other components of the MD 200 (e.g., controller 210, processor 215, memory 217, communication unit 260, therapy modification module 285, therapy termination module 295, or the like). Body data in analog form may be also used in one or more embodiments.

Turning now to FIG. 3B, an MD 200 (as described above in FIG. 3) is provided, in accordance with one illustrative embodiment of the present disclosure. FIG. 3B depicts the body data units of FIG. 3A, (i.e., [360-370], [373-376]), in accordance a different embodiment in which they are included within the MD 200, instead of being externally coupled to the MD 200 as shown in FIG. 3A. In accordance with various embodiments, any number and type of body data units (FIGS. 3A & 3B, [360-370], [373-376]) may be included within the MD 200 as shown in FIG. 3B, while other body data units may be externally coupled, as shown in FIG. 3A. The body data units may be coupled to the body data collection module 287 in a fashion similar to shown and discussed with respect to FIG. 3A, or in other ways used in coupling intra-medical device modules and units. It should be noted that the manner by which the body data units may be coupled to the body data collection module 287 is not essential to and does not limit the embodiments described herein.

Turning now to FIG. 4, a stylized depiction of the therapy termination unit 295 is illustrated in accordance with one embodiment of the present disclosure. The therapy termination unit 295 comprises a therapy timing unit 410 and a signal termination unit 440. The blocks illustrated in FIG. 4 may represent a hardware unit, a firmware unit, a software unit, and/or a combination any one thereof.

The therapy termination unit 295 may receive data from the efficacy determination module 266, which may provide information as to the extent of efficacy resulting from the therapy delivered by the MD 200. Based upon the efficacy information, the MD 200 may determine that sufficient efficacy has been achieved such that the present therapy being delivered may be terminated. In one embodiment, once sufficient efficacy has been achieved (e.g., by a cardiac index exceeding or crossing a cardiac efficacy threshold), it may be advantageous to terminate the therapy. This may reduce the possibility of re-excitement or re-triggering of undesirable brain activity that may occur if the therapy signal continues to be applied to target tissue after the therapy has reduced or terminated the undesirable brain activity, or an efficacy index crosses an efficacy threshold. Current electrical stimulation therapies, for example, generally fail to consider the possibility that therapy efficacy may be dose-dependent and/or time-dependent at microscopic or macroscopic timescales, such that continuing to provide therapy after achieving a desired efficacious effect may lead to undesirable effects, including reversal or destruction of the efficacious effect. Typical closed-loop neurostimulation therapies provide a therapy having a pre-programmed duration, with no consideration of reducing the duration if efficacy is achieved prior to the elapse of the full programmed duration. In addition, energy savings may be realized by terminating therapy delivery as soon as practicable after determining that a desired level of efficacy has been achieved, thus preserving and/or extending the battery life of the MD 200.

Accordingly, once a sufficient level of efficacy has been identified, it may be beneficial to terminate the therapy, even in mid-signal application of a therapy signal that would be applied for a longer duration absent the timely identification of an efficacious effect. The therapy timing unit 410 may be capable of determining a cut-off time point to terminate, substantially terminate, or modify the therapy, which otherwise may be continued until a default or programmed duration is reached if no attempt is made to identify an efficacious effect. Based upon data from the efficacy determination module 266, the therapy timing unit 410 may be capable of determining a time point at which to terminate (that is, stop applying to the target structure) the therapy signal.

Based upon the timing of the therapy termination determined by the therapy timing unit 410, in some embodiments the therapy determination unit 295 may determine an amount of charge to apply to one or more electrodes to achieve charge balance where charge-balanced stimulation is employed. Techniques known in the art for providing charge-balanced electrical stimulation may be used in the therapy determination unit, and the unit may provide active and/or passive charge balancing to a plurality of electrodes. In some embodiments, charge balancing may be handled by hardware and/or software associated with the therapy module 275.

Once the time point of terminating the therapy signal is determined, the signal termination unit 440 may terminate the signal at the appropriate time.

In some embodiments, terminating the therapy may comprise terminating a therapy after delivery of a complete pulse as defined by one or more programmed parameters (see FIGS. 8A-B). For example, where an efficacious effect is detected between programmed pulses in a closed-loop therapy, therapy timing unit 410 may determine to terminate therapy immediately upon receiving the signal, and signal termination unit 440 may interrupt the therapy unit 275 to prevent delivery of the next programmed pulse (FIGS. 8A-B). In other embodiments, terminating the therapy may comprise terminating a programmed pulse prior to the elapse of its programmed pulse width. For example, where an efficacious effect is detected during the delivery of a programmed pulse in a closed-loop therapy, timing unit 410 may determine to terminate therapy immediately and signal termination unit 440 may interrupt the therapy unit 275 to terminate the pulse prior to the elapse of its programmed pulse width (FIGS. 7A-B). Appropriate steps may be taken to ensure charge-balancing to avoid damage to electrodes, or to extend therapy for short periods (e.g., a ramp-down period) to avoid undesirable effects upon tissue associated with immediate termination of therapy. For example, tissue integrity may be monitored by measuring responses to various stimuli and/or by monitoring tissue stress markers.

FIGS. 5-8 illustrate various stylized pulsed therapy signals that may be terminated by the therapy termination unit 295.

The therapy termination unit 295 may terminate a pulse burst signal prior to the programmed end time (commonly referred to as the "on time") of the pulse. The programmed pulse burst of 710 (FIG. 5A) may be terminated, resulting in a shortened pulse burst 720 (FIG. 5A) after determining that an efficacious effect was detected. Similarly, the pulse burst 810 (FIG. 6A) may be terminated prior to the delivery of the next programmed pulse, but may complete any necessary charge balancing. In FIG. 6, the charge-balancing phases of the pulses are shown (they are omitted in FIG. 5 for simplicity). The efficacious result is detected during the charge-balancing phase. As shown in FIG. 6B, the therapy termination unit 295 may complete the charge-balancing phase of the pulse already in progress (whose initial phase was completed prior to the detection of the efficacious result), and may terminate the signal by not applying the remaining programmed pulses, shown in FIG. 6A.

Turning now to FIGS. 7-8, FIG. 7A illustrates an exemplary therapy signal that includes a pulse 510, which may be one pulse in a therapy comprising multiple pulses, or a single pulse. During the application of pulse 510 to a target tissue, the efficacy determination module 266 may determine that sufficient efficacy has been reached, such as by the detecting a particular efficacious effect identified by an efficacy index reaching or crossing an efficacy threshold. The therapy termination unit 295 may then determine that the therapy signal 510 is to be terminated at a time after the efficacious effect is detected. As exemplified in FIG. 7B, the signal termination unit 440 may terminate the signal 510 by shortening the pulse width (520) based upon the termination timing determined by therapy timing unit 410.

FIG. 8 illustrates another exemplary therapy signal that includes a pulse signal 610. During the administration of the pulse signal 610, the efficacy determination module 266 may determine that sufficient efficacy has been reached. Therapy termination unit 295 may determine that the therapy signal 610 is to be terminated at a time after an efficacious effect is detected, resulting in a shortened pulse signal 620. The MD 200 may provide an active (FIG. 8C) and/or a passive (FIG. 8B) charge balancing region 630 in order to terminate the pulse 610, and maintain adequate charge balance. In another embodiment, therapy termination unit 295 may determine that the entire pulse 610 should be delivered to the target tissue (FIG. 8A). Charge-balancing may not be effected in certain embodiments or it may be delayed. Known techniques for implementing charge balancing among two or more electrodes can be used to reduce damage to tissue, to electrodes, or both.

FIGS. 10A-10C illustrate an exemplary therapy signal that may be modified based upon feedback relating to the disease or symptom/manifestation being treated by the therapy. The therapy modification unit 285 may determine that the programmed or planned therapy signal 910 (FIG. 10A) should be modified based upon determination of an efficacious result. In response to this determination the therapy modification unit 285 may reduce the duration of the pulse signal, resulting in a modified pulse signal 1020 (FIG. 10B). Alternatively, in response to the determination made by the therapy modification unit 285 that the therapy signal should be boosted, the unit 285 may increase or boost the duration of the pulse signal, resulting in yet another modified pulse signal 1030 (FIG. 10C). While FIG. 10 illustrates modification of the pulse width of the pulse, it will be appreciated that other parameters defining the signal (e.g., pulse shape, current amplitude, pulse frequency, inter-pulse interval, pulse burst duration, total number of pulses in a burst), could also be the subject of modification by the therapy modification unit 285.

FIG. 11 shows a flowchart depiction of a method, in accordance with one illustrative embodiment of the present disclosure. In the depicted method, an epileptic event may be detected at 1110. In one exemplary embodiment, detecting the epileptic event may comprise detecting at least one of a cardiac index, a body movement/kinetic index, a respiratory index, and a responsiveness/awareness index indicative of an epileptic event. After the detecting the event at 1110, therapy may be applied to at least one target tissue (e.g., neural) of the patient at 1120.

The therapy may be applied at any time during the epileptic event. In one embodiment, the therapy may be applied at a downslope zero crossing of at least one neuronal activity wave of the brain of said patient, as determined from a cortical/neuronal electrical (e.g., EEG signal) thermal or optical signal. In another embodiment, the therapy may be applied when a ratio of a short-term and a long-term measure of HR exceeds a threshold.

In an exemplary embodiment, the therapy may be an electrical therapy, comprising one or more electrical pulses. The electrical therapy may comprise an electrical signal having a number of parameters discussed above. In one embodiment, an electrical signal may have a programmed on-time. In one embodiment, an electrical pulse may have a programmed pulse width and a programmed current amplitude.

The target tissue (e.g., neural structure) to which therapy may be applied may be at least one of the patient's brain, a target portion of the patient's brain, a cranial nerve of the patient, or a target portion of the cranial nerve of the patient. In one embodiment, an electrical therapy may be applied to a first target area in at least one of a brain region or a cranial nerve of the patient. Exemplary brain regions may include a frontal lobe, a temporal lobe, an amygdala, and a hippocampus. Exemplary cranial nerves may include a vagus nerve, a trigeminal nerve, a hypoglossal nerve, an olfactory nerve, and a glossopharyngeal nerve, and branches and combinations of the foregoing.

Thereafter, a body signal indicative of the patient's response to the therapy may be received at 1130. In preferred embodiments, the response comprises a measure, value or index indicative of an effect of the therapy on the epileptic event. In one embodiment, the body signal may be an autonomic signal. In another embodiment, the body signal may be a neurologic signal (e.g., cognitive). In one embodiment, the body signal may be a metabolic signal. In another embodiment, the body signal may be an endocrine signal. In one embodiment, the body signal may be a tissue stress marker signal. The body signal may be selected from one or more of the foregoing.

Exemplary autonomic signals that may be detected include, but are not limited to, a cardiac signal, a skin resistance signal, a body temperature (e.g., a core temperature or a temperature of a target tissue or organ), or an infrared activity of a portion of the patient's body, among others.

Exemplary neurologic signals that may be detected include, but are not limited to, a motor activity signal or an evoked response signal, among others. In one embodiment, the motor activity signal is recorded with an accelerometer from one or more body locations. The accelerometer output may be used to determine one or more body movement measures/indices (e.g., direction, velocity, magnitude of acceleration). Body posture, which also provides information about the patient's state, may be obtained using from an accelerometer or inclinometer.

Exemplary metabolic signals that may be detected include, but are not limited to, serum glucose, blood pH, a lactic acid concentration of the patient's blood, a pyruvic acid concentration of the patient's blood, or a potassium concentration of the patient's blood, among others.

Exemplary cognitive signals that may be detected include, but are not limited to, signals indicative of response to a responsiveness test and an awareness test. This may include, for example, a signal indicative of a response to one of a simple reaction time test and a complex reaction time test. Other exemplary cognitive signals include signals indicative of response to one or more of a memory test, a language test, an IQ test, and an alertness test. Other cognitive tests may also be used to generate cognitive signals for use in embodiments of the present disclosure.

Various signals that may be detected are summarized in the following table:

TABLE 1

| Multimodal Signals |
|---|
| Autonomic |

Cardiac: EKG, PKG, Echocardiography, Apexcardiography (ApKG), Intra-cardiac pressure, Cardiac blood flow, cardiac thermography; from which can be derived, e.g., heart rate (HR), change of HR, rate of change of HR, heart rate variability (HRV), change of HRV, rate of change of HRV, HRV vs. HR. Also, blood pressure, heart sounds, heart rhythm, heartbeat wave morphology, heartbeat complex morphology, and thoracic wall deflection.
Vascular: Arterial Pressure, Arterial and venous blood wave pressure morphology; Arterial and venous blood flow velocity, arterial and venous blood flow sounds, arterial and venous TABLE 1-continued Multimodal Signals thermography
Respiratory: Frequency, tidal volume, minute volume, respiratory wave morphology,
respiratory sounds, end-tidal CO2, Intercostal EMG, Diaphragmatic EMG, chest wall and
abdominal wall motion, from which can be derived, e.g., respiration rate (RR), change of
RR, rate of change of RR. Also, arterial gas concentrations, including oxygen saturation, as
well as blood pH can be considered respiratory signals.
Dermal: Skin resistance, skin temperature, skin blood flow, sweat gland activity
Concentrations of catecholamines (and their metabolites) and acetylcholine or
acetylcholinesterase activity in blood, saliva and other body fluids concentrations and
its rate of change.
Neurologic Cognitive/behavioral: Level of consciousness, attention, reaction time, memory, visuo-
spatial, language, reasoning, judgment, mathematical calculations, auditory and/or visual
discrimination
Kinetic: Direction, speed/acceleration, trajectory (1D to 3D), pattern, and quality of
movements, force of contraction, body posture, body orientation/position, body part
orientation/position in reference to each other and to imaginary axes, muscle tone, agonist-
to-antagonist muscle tone relation, from which can be derived, e.g., information about gait,
posture, accessory movements, falls
Vocalizations: Formed, unformed
EEG/ECoG, Evoked potentials, field potentials, single unit activity
Endocrine: Prolactin, luteinizing hormone, follicle stimulation hormone, growth hormone,
ACTH, cortisol, vasopressin, beta-endorphin, beta, lipotropin.-, corticotropin-releasing
factor (CRF)
Stress Markers: Reactive oxygen and nitrogen species including but not limited to iso- and
neuro-prostanes and nitrite/nitrate ratio, gluthatione, gluthatione disulfide and gluthatione
peroxidase activity, citrulline, protein carbonyls, thiobarbituric acid, the heat shock
protein family, catecholamines, lactic acid, N-acetylaspartate, and metabolites of any of
the foregoing.
Metabolic: arterial pH and gases, oxygen consumption, lactate/pyruvate ratio, electrolytes, glucose Certain signals may be listed under more than one class. For example, pH is listed under Autonomic since it is under respiratory control and also under Metabolic since it is also influenced by metabolic by-products.

A determination may then be made at 1140 whether the body signal indicates an efficacious effect of the therapy on the epileptic event. As discussed above, an "efficacious effect" may be demonstrated by a change in an efficacy index, an observation of improvement or termination of the epileptic event, or the like.

In one embodiment, the determination at 1140 may comprise determining an efficacy index based upon said responsive body signal.

An efficacious effect and/or an efficacy index may be determined at any time during or after application of the therapy at 1120. The effect and/or the efficacy index may be determined as described above in reference to FIG. 2. In some embodiments, one or more efficacy indices are continuously or discretely monitored following delivery of the therapy to the patient to provide a timely termination or modification of said therapy, and in some embodiments continuous. In some embodiments, an efficacy index may be determined after applying the electrical therapy at 1120 for a predetermined duration. For another example, an efficacy index may be determined after applying the electrical therapy at 1120 for less than a predetermined duration.

If an efficacious effect is indicated, further application of therapy may be terminated at 1145. For example, an efficacious effect may be indicated by a finding the efficacy index may be equal to or greater than an efficacy threshold.

If the therapy comprises at least one electrical pulse, terminating the therapy may comprise not delivering another pulse. Alternatively or in addition, terminating a therapy comprising at least one electrical pulse having a programmed pulse width may comprise terminating delivery of the electrical pulse prior to the end of the programmed pulse width.

If an efficacious effect is not indicated, the application of the therapy may be continued, as shown in FIG. 11 by the flow line from 1140 to 1120. For example, a lack of an efficacious effect may be indicated by a finding the efficacy index may be less than an efficacy threshold, and the therapy may be continued in response to such a finding.

In one embodiment, the therapy may be continued until the lapse of a programmed time period if at least two attempts at terminating it are temporally correlated with relapse of the seizure. In another embodiment, the therapy may be continued for a predetermined duration. The predetermined duration may comprise a default electrical stimulation therapy to be applied to a target tissue(s) following detection of an epileptic event such as a seizure. The duration may be selected to result in termination of the application of the therapy after a safety duration, which may reduce the likelihood of injury to the tissue to which the therapy is applied, and/or preserve battery life. In another embodiment, if an adverse effect of the therapy is detected, termination may be based on analysis of the risk/benefit ratio; if the consequences of terminating the therapy are more serious that the adverse effects of said therapy, the therapy may be continued. Otherwise, it may be discontinued.

In one embodiment, if an efficacious effect is not determined, the therapy may be modified at 1150. If the therapy is an electrical therapy, modifying the therapy may comprise modifying at least one parameter defining or relating to the therapy, such as pulse width, current amplitude, pulse frequency, voltage amplitude, pulse waveform, pulse burst duration, total number of pulses, number of pulses per unit time, inter-pulse interval, pulse phase, number of phases in a pulse, number of phases in a pulse burst, polarity of pulse phase, current density per pulse, and a total current density for a pulse burst. Parameters relating to the interaction of the signal and the body of the patient may also be adjusted, such as a timing of therapy delivery (e.g., relative to a zero-crossing, an extrema, or a region of ascending or descending slope of the body signal(s) used to determine efficacy, such as a neuronal or other biologic oscillation).

The modifying may comprise modifying the parameter as a function of at least one of an efficacy index value or a direction of change of an efficacy index value. In one embodiment, the duration of the therapy may be adaptively determined, based on the efficacy index. For example, a high efficacy index, which may be indicative of full or substantial cessation or termination of epileptic activity, may be used to adaptively determine the duration of therapy by terminating the therapy. On the other hand, a low efficacy index, which may be indicative of continuing epileptic activity, may be used to adaptively determine the therapy should continue. In addition to duration, other parameters defining the therapy may be adaptively adjusted based upon the efficacy index.

In other embodiments, modifying a therapy may be performed according to a predetermined schedule, in response to an external input, or both, alone or in combination with any other modifying technique.

In one embodiment, if the therapy has a predetermined duration, modifying the therapy at 1150 may be performed prior to the end of the predetermined duration.

If modifying is performed at 1150, flow may return to applying a therapy (such as a modified therapy) at 1120.

FIG. 12 shows a flowchart depiction of a method, in accordance with one illustrative embodiment of the present disclosure. FIG. 12 contains many elements in common with FIG. 11, and these common elements need not be discussed again. In the method depicted in FIG. 12, the therapy signal applied at 1322 has a programmed on-time.

Upon application of the therapy signal, at least one of a brain signal (e.g., responsiveness as measured using a complex response time test, EEG), an autonomic signal (e.g., heart rate, EKG morphology, body/organ temperature), a metabolic signal (e.g., glucose, oxygen consumption), an endocrine signal (e.g., cortisol), or a tissue stress marker signal (e.g., CK) may be detected at 1332. The signal detected at 1332 may be used in a determining at 1342 whether the at least one signal indicates that the therapy has an efficacious effect. Determination of efficacy may be performed on at least one of a microscopic, mesoscopic or macroscopic time scales (as defined herein) using signals whose rate of change befits the time scale. Electrical neuronal, motor (e.g., limb, ocular) activity may change on a microscopic time scale; heart rate, respiratory rate and certain metabolic, cognitive and tissue stress marker signals may change on a mesoscopic or macroscopic scale and others such as memory, quality of life and heart rate variability may change on a macroscopic time scale.

In the embodiment depicted in FIG. 12, upon a determination at 1342 that the therapy has an efficacious effect, the application of the electrical signal may be terminated prior to the elapse of said programmed on-time, at 1347. The effect of therapy may also be manifest at a plurality of time scales, e.g., the effect may be temporally correlated with the therapy in a first effect, resulting in, e.g., immediate interruption of the seizure (within milliseconds to seconds), and may also have a second effect that outlasts the duration of therapy delivery (e.g., a carryover effect or an effect that is not manifested until some time after the termination of therapy delivery). For example, effects of non-contingent vagus nerve stimulation may not be significantly manifest until six or more months after implantation of the device, but a given seizure event may be immediately terminated upon delivery of a therapy two months after implantation.

In the embodiment depicted in FIG. 12, upon a determination at 1342 that the therapy lacks an efficacious effect, flow may return to applying the electrical signal at 1322. Alternatively or in addition, the therapy may be modified at 1357. Modification at 1357 may comprise any technique discussed herein. In one embodiment, modification at 1357 may be based on a statistical metric of a seizure sample, wherein said seizure sample is one of a patient-specific seizure population or a reference seizure population.

Any method depicted in FIGS. 11-12 may be performed by a non-transitive, computer-readable storage device for storing instructions that, when executed by a processor, perform the method.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

In various embodiments, the present disclosure relates to the following numbered paragraphs:

21. A non-transitive, computer-readable storage device for storing data that when executed by a processor, perform a method, comprising:

detecting an epileptic event in a patient based on at least one of a cardiac index, a kinetic index, and a responsiveness index of the patient;

applying an electrical signal therapy to a neural structure of the patient in response to said detecting;

detecting at least one body signal after applying said electrical signal therapy, wherein said at least one body signal is selected from an autonomic signal, a neurologic signal, a metabolic signal, an endocrine signal, or a tissue stress marker signal; and determining an efficacy index based upon said feedback body signal;

wherein the duration of the therapy is adaptively determined based on the efficacy index.

22. The non-transitive, computer-readable storage device of numbered paragraph 21, wherein:

detecting said autonomic signal comprises detecting at least one of a cardiac signal, the patient's body temperature, or an infrared activity of a portion of said patient's body;

detecting said neurologic signal comprises detecting at least one of a motor activity signal, a brain electrical activity signal, an awareness signal, and a responsiveness signal; or detecting said metabolic signal comprises detecting at least one of an arterial gas signal, a pH value of said patient's blood, an oxygen consumption, a lactic acid concentration of said patient's blood, a pyruvic acid concentration of said patient's blood, or a potassium concentration of said patient's blood.

23. The non-transitive, computer-readable storage device of numbered paragraph 21, wherein applying said electrical signal therapy comprises at least one of applying a single pulse, or applying a burst of pulses.

24. The non-transitive, computer-readable storage device of numbered paragraph 21, wherein said efficacy index is based upon a change in a number of body signals affected by the electrical therapy.

25. The non-transitive, computer-readable storage device of numbered paragraph 21, wherein said efficacy index is based upon comparing a pattern of seizure spread to a reference pattern of seizure spread.

26. A non-transitive, computer-readable storage device for storing data that when executed by a processor, perform a method, comprising:
  detecting a first epileptic seizure in a patient;
  applying a first electrical signal therapy having a programmed on-time to at least one neural structure of said patient for treating said first epileptic seizure;
  detecting at least one body signal after applying the electrical signal therapy, wherein said body signal is selected from a cardiac signal, a movement signal, a body temperature signal, a responsiveness signal, an awareness signal, an arterial gas signal, an ocular signal, or an electrodermal signal
  determining whether said at least one body signal indicates that said electrical signal therapy has an efficacious effect; and
  terminating the application of said electrical signal therapy in response to a determination that said electrical signal therapy has an efficacious effect, wherein said termination occurs prior to the elapse of said programmed on-time, and
  not resuming the application of said electrical signal therapy until the occurrence of an event selected from detecting a worsening of the first epileptic seizure, detecting a relapsing of the first epileptic seizure, detecting an end of the first epileptic seizure, the elapse of a re-initiation time period after the termination of the therapy, detecting the onset of a second epileptic seizure, and determining that a cumulative seizure severity index has been reached, determining an indication that a cumulative seizure frequency index has been reached, determining that resumption of said electrical therapy does not exceed a predetermined stimulation limit, determining that application of the electrical therapy will not result in an adverse effect, and determining that a beneficial carryover effect has lapsed.

33. A method, comprising:
  detecting a first epileptic seizure in a patient based on at least one of a cardiac index, a kinetic index, and a responsiveness index of the patient;
  applying an electrical therapy to a first target tissue in response to detecting the first seizure, wherein the first target tissue is at least one of a brain region or a cranial nerve selected from a vagus nerve, a trigeminal nerve, a hypoglossal nerve, and a glossopharyngeal nerve;
  receiving a body signal selected from an autonomic signal, a neurologic signal, a metabolic signal, an endocrine signal, or a tissue stress marker signal;
  determining whether said body signal indicates that said electrical therapy has an efficacious effect in a time window;
  terminating the application of said electrical therapy if the response indicates that the electrical therapy has an efficacious effect; and
  not resuming application of the electrical therapy until the occurrence of an event selected from a worsening of the first epileptic seizure, a relapsing of the first epileptic seizure, an end of the first epileptic seizure, the elapse of a re-initiation time period after the termination of the therapy, an onset of a second epileptic seizure, receiving an indication that a cumulative seizure severity index has been reached, receiving an indication that a cumulative seizure frequency index has been reached, receiving an indication that resumption of said electrical therapy does not exceed a predetermined stimulation limit, an indication that application of the electrical therapy will not result in an adverse effect, and receiving an indication of the lapse of a beneficial carryover effect.

34. The method of numbered paragraph 33, wherein said time window is a time window having a duration selected from: less than 10 seconds, less than 5 seconds, less than 4 seconds, less than 3 seconds, less than 2 seconds, less than 1 second, less than 500 milliseconds, less than 250 milliseconds, less than 100 milliseconds, or less than 50 milliseconds.

35. The method of numbered paragraph 33, wherein said time window is at least one of a microscopic time scale, a mesoscopic time scale, or a macroscopic time scale.

36. The method of numbered paragraph 33, wherein said time window is a function of the inherent time scale of change of the body signal.

37. A medical device system, comprising:
  an epileptic seizure detection module configured to detect a first epileptic seizure based on at least one of a cardiac index and a kinetic index;
  a therapy module configured to apply a therapy to at least one neural structure of said patient based on an indication of said epileptic seizure;
  at least one sensor configured to collect at least one of cardiac signals, body movement signals, cognitive signals, or brain electrical activity signals from a patient's body;
  an efficacy determination module configured to receive said collected one or more body signals and detect a response of said epileptic event to said therapy, wherein said detection is based on said collected one or more body signals; and
  a therapy termination module configured to terminate said therapy based on an indication that said therapy has an efficacious effect, and to prohibit the application of the therapy until the occurrence of an event selected from a worsening of the first epileptic seizure, a relapsing of the first epileptic seizure, an end of the first epileptic seizure, the elapse of a re-initiation time period after the termination of the therapy, an onset of a second epileptic seizure, receiving an indication that a cumulative seizure severity index has been reached, receiving an indication that a cumulative seizure frequency index has been reached, receiving an indication that resumption of said electrical therapy does not exceed a predetermined stimulation limit, an indication that application of the electrical therapy will not result in an adverse effect, and receiving an indication of the lapse of a beneficial carryover effect.

101. A method, comprising:
  detecting an epileptic event in a patient based on at least one detection body signal selected from at least one of an autonomic signal, a neurologic signal, a metabolic signal, an endocrine signal, and a tissue stress marker signal;
  initiating at least one safety precaution in response to said detection of said epileptic event;
  applying an electrical therapy to a first target tissue in at least one of a brain region or a cranial nerve of said patient in response to said detecting the event;
  receiving an efficacy body signal after applying the electrical therapy, wherein said efficacy body signal is selected from at least one of an autonomic signal, a neurologic signal, a metabolic signal, an endocrine signal, and a tissue stress marker signal;

determining whether said efficacy body signal indicates that said electrical therapy has an efficacious effect; and terminating said at least one safety precaution if the determining indicates that the electrical therapy has an efficacious effect.

102. The method of numbered paragraph 101, wherein the determination of efficacy is made on at least one temporal scale 103. The method of numbered paragraph 101, wherein said at least one safety precaution is terminated based on at least one of the magnitude of the temporal scales at which efficacy of therapy occurs or the body signal used for determination of said efficacy.

104. The method of numbered paragraph 101, further comprising logging the time at which said at least one safety precaution is terminated and at least one parameter of said efficacy body signal.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

What is claimed:

1. A medical device system, comprising:
   an epileptic seizure detection module via one or more processors configured to detect a first epileptic seizure based on a first body signal having a rapid rate of change and a second body signal having a slow rate of recovery;
   a therapy module via the one or more processors configured to apply a therapy to at least one neural structure of a patient based on a detection of the first epileptic seizure;
   an efficacy determination module via the one or more processors configured to detect a beneficial response of the body signal with the rapid rate of change and of the body signal with the slow rate of recovery, wherein efficacy is determined based on a comparison to one or more efficacy thresholds; and
   a therapy termination module via the one or more processors configured to terminate the therapy based on an indication that the therapy has a beneficial effect and to prohibit an application of the therapy until a second epileptic seizure detection;
   wherein the body signal with the rapid rate of change is one of: a brain electrical activity index or a cardiac activity index and the body signal with the slow rate of recovery is one of: a level of consciousness; an attention; a reaction time; a memory; a visuo-spatial; a language; a reasoning; a judgment; mathematical calculations, an auditory and/or visual discrimination; a blood arterial pH; blood gases; a lactate/pyruvate ratio; electrolytes; a lactic acid concentration; and a prolactin.

2. The medical device system of claim 1, further comprising an adverse effect determination module configured to receive the first body signal or the second body signal and detect an adverse effect of the therapy based on the first body signal or the second body signal.

3. The medical device system of claim 1, further comprising:
   a therapy modification module configured to modify at least one parameter of the therapy, based on an indication that a therapy response is not indicative of an efficacious effect or is indicative of an adverse effect; and
   wherein the therapy module is configured to apply a modified therapy to at least one neural structure of the patient or to terminate the therapy.

4. The medical device system of claim 3, wherein the therapy is an electrical therapy, and modifying the at least one parameter comprises modifying a parameter selected from a group consisting of a waveform, a pulse width, a total number of pulses, a number of pulses per unit time, a frequency of pulses per unit time, an inter-pulse interval, an amplitude, a phase, number of phases in a pulse, a number of phases in a pulse train, a polarity of pulse phase, a current density per pulse, a total current density for a pulse train, a degree of isotropy of current flow, a time delay between a delivery of a current and an arrival of the current at a body target, a timing of the therapy delivery relative to a zero-crossing of an efficacy body signal, a timing of the therapy delivery relative to an extremum occurrence of the efficacy body signal, or a timing of the therapy delivery relative to a region of an ascending or descending slope of a body signal.

5. The medical device system of claim 1, wherein the therapy is one or more of an electrical therapy, a magnetic therapy, a chemical therapy, a heating or cooling therapy, applying a positive or negative pressure to a target tissue, an optical therapy, a cognitive therapy, a sensory therapy, or a motor therapy.

6. The medical device system of claim 1, wherein a beneficial response to the therapy of the body signal with the slow rate of recovery is indicative of a prevention of an occurrence of clinical manifestations.

\* \* \* \* \*